(12) United States Patent
Short et al.

(10) Patent No.: US 9,951,025 B2
(45) Date of Patent: Apr. 24, 2018

(54) HALOGENOPYRAZOLES AS INHIBITORS OF THROMBIN

(71) Applicant: VERSEON CORPORATION, Fremont, CA (US)

(72) Inventors: Kevin Michael Short, Fremont, CA (US); Son Minh Pham, Fremont, CA (US); David Charles Williams, Fremont, CA (US)

(73) Assignee: VERSEON CORPORATION, Fremont, CA (US)

( * ) Notice: Subject to any disclaimer, the term of this patent is extended or adjusted under 35 U.S.C. 154(b) by 0 days.

(21) Appl. No.: 14/776,641

(22) PCT Filed: Mar. 17, 2014

(86) PCT No.: PCT/US2014/000058
§ 371 (c)(1),
(2) Date: Sep. 14, 2015

(87) PCT Pub. No.: WO2014/149139
PCT Pub. Date: Sep. 25, 2014

(65) Prior Publication Data
US 2016/0046585 A1 Feb. 18, 2016

Related U.S. Application Data

(60) Provisional application No. 61/789,358, filed on Mar. 15, 2013, provisional application No. 61/899,588, filed on Nov. 4, 2013.

(51) Int. Cl.
| | |
|---|---|
| *A61K 31/4155* | (2006.01) |
| *A61K 31/5377* | (2006.01) |
| *A61K 31/4439* | (2006.01) |
| *C07D 231/38* | (2006.01) |
| *C07D 409/12* | (2006.01) |
| *C07D 233/88* | (2006.01) |
| *C07D 401/04* | (2006.01) |
| *C07D 409/14* | (2006.01) |

(52) U.S. Cl.
CPC ........ *C07D 231/38* (2013.01); *A61K 31/4155* (2013.01); *A61K 31/4439* (2013.01); *A61K 31/5377* (2013.01); *C07D 233/88* (2013.01); *C07D 401/04* (2013.01); *C07D 409/12* (2013.01); *C07D 409/14* (2013.01)

(58) Field of Classification Search
None
See application file for complete search history.

(56) References Cited

U.S. PATENT DOCUMENTS

| | | |
|---|---|---|
| 3,250,761 A | 5/1966 | Schmidt et al. |
| 3,926,999 A | 12/1975 | Poetsch |
| 4,008,249 A | 2/1977 | Fischer et al. |
| 4,160,452 A | 7/1979 | Theeuwes |
| 4,256,108 A | 3/1981 | Theeuwes |
| 4,265,874 A | 5/1981 | Bonsen et al. |
| 5,466,823 A | 11/1995 | Talley et al. |
| 5,547,978 A | 8/1996 | Christensen et al. |
| 5,739,083 A | 4/1998 | Endo et al. |
| 5,753,688 A | 5/1998 | Talley et al. |
| 5,902,852 A | 5/1999 | Schulz et al. |
| 5,916,908 A | 6/1999 | Giese et al. |
| 6,114,358 A | 9/2000 | Baucke et al. |
| 6,589,997 B2 | 7/2003 | Pillarisetti et al. |
| 6,962,905 B1 | 11/2005 | Gustafsson |
| 7,625,944 B2 | 12/2009 | Sinha et al. |
| 8,188,045 B2 | 5/2012 | Blair et al. |
| 9,371,307 B2 | 6/2016 | Freire et al. |
| 2002/0055639 A1 | 5/2002 | Nebel et al. |
| 2002/0091116 A1 | 7/2002 | Zhu et al. |
| 2003/0144309 A1 | 7/2003 | Choon-Moon |
| 2004/0132726 A1 | 7/2004 | Arora et al. |
| 2005/0009827 A1 | 1/2005 | Nazare et al. |
| 2005/0065144 A1 | 3/2005 | Feng et al. |
| 2005/0203127 A1 | 9/2005 | Cezanne et al. |
| 2008/0188527 A1 | 8/2008 | Cashman |
| 2008/0275070 A1 | 11/2008 | Liu et al. |
| 2009/0105253 A1 | 4/2009 | Kubo et al. |
| 2009/0163545 A1 | 6/2009 | Goldfarb |
| 2010/0210696 A1 | 8/2010 | Nishida et al. |
| 2011/0071289 A1* | 3/2011 | Horiuchi ............... C07D 231/38 544/238 |

(Continued)

FOREIGN PATENT DOCUMENTS

| | | |
|---|---|---|
| CN | 101851207 A | 10/2010 |
| EP | 0246888 A2 | 11/1987 |
| EP | 0854723 A1 | 7/1998 |
| EP | 088358 B1 | 3/2004 |
| JP | S50-117936 A | 9/1975 |
| JP | H01226815 A | 9/1989 |
| JP | H10-509708 A | 9/1998 |
| JP | 2006511608 A | 4/2006 |
| JP | 2007506741 A | 3/2007 |
| JP | 2007511485 A | 5/2007 |
| JP | 2011520967 A | 7/2011 |
| RU | 2221808 C2 | 1/2004 |
| WO | 1996014843 A2 | 5/1996 |
| WO | 1998018792 A1 | 5/1998 |
| WO | 1998025930 A2 | 6/1998 |

(Continued)

OTHER PUBLICATIONS

Database Registry Chemical Abstracts Service, Columbus, Ohio, Accession No. RN 67897-88-5, Entered STN: Nov. 16, 1984.*

(Continued)

Primary Examiner — Samantha L Shterengarts
(74) Attorney, Agent, or Firm — Davis Wright Tremaine, LLP

(57) ABSTRACT

There are provided inter alia multisubstituted aromatic compounds useful for the inhibition of thrombin, which compounds include substituted pyrazolyl. There are additionally provided pharmaceutical compositions. There are additionally provided methods of treating and preventing a disease or disorder, which disease or disorder is amenable to treatment or prevention by the inhibition of thrombin.

52 Claims, No Drawings

(56) References Cited

U.S. PATENT DOCUMENTS

| | | | |
|---|---|---|---|
| 2012/0110702 A1* | 5/2012 | Yap | A61K 45/06 800/298 |
| 2012/0264798 A1 | 10/2012 | Sinha et al. | |
| 2013/0040950 A1 | 2/2013 | Short et al. | |
| 2016/0136177 A1 | 5/2016 | Short et al. | |
| 2016/0256440 A1 | 9/2016 | Short et al. | |

FOREIGN PATENT DOCUMENTS

| | | | |
|---|---|---|---|
| WO | 9828269 A1 | 7/1998 | |
| WO | 199842698 A1 | 10/1998 | |
| WO | 2000009500 A2 | 2/2000 | |
| WO | 00041716 A1 | 7/2000 | |
| WO | WO 2000/071536 | * | 11/2000 |
| WO | 0112189 A1 | 2/2001 | |
| WO | 2001040223 A2 | 2/2001 | |
| WO | 2001019798 A2 | 3/2001 | |
| WO | 2002000651 A2 | 1/2002 | |
| WO | 02092573 A2 | 11/2002 | |
| WO | 03048155 A1 | 6/2003 | |
| WO | 03061682 A1 | 7/2003 | |
| WO | 03062206 A2 | 7/2003 | |
| WO | 2004000785 A2 | 12/2003 | |
| WO | 2004035564 A1 | 4/2004 | |
| WO | 2004058721 A2 | 7/2004 | |
| WO | 2004058722 A1 | 7/2004 | |
| WO | 2004089911 A1 | 10/2004 | |
| WO | 2004098589 A1 | 11/2004 | |
| WO | 2005023761 A2 | 3/2005 | |
| WO | 2006074445 A2 | 7/2006 | |
| WO | 2006108643 A2 | 10/2006 | |
| WO | 2007067836 A2 | 6/2007 | |
| WO | 2008009638 A2 | 1/2008 | |
| WO | 2008016883 A2 | 2/2008 | |
| WO | 2008062739 A1 | 5/2008 | |
| WO | 2008064265 A2 | 5/2008 | |
| WO | 2008079277 A1 | 7/2008 | |
| WO | 2008105383 A1 | 9/2008 | |
| WO | 2009010560 A1 | 1/2009 | |
| WO | 2009041447 A1 | 4/2009 | |
| WO | 2009097141 A1 | 8/2009 | |
| WO | 2009100438 A2 | 8/2009 | |
| WO | 2009140621 A2 | 11/2009 | |
| WO | 2010005580 A2 | 1/2010 | |
| WO | 2010020600 A1 | 2/2010 | |
| WO | 2010020601 A1 | 2/2010 | |
| WO | 2010020602 A1 | 2/2010 | |
| WO | 2010127855 A1 | 11/2010 | |
| WO | 2012065019 A2 | 5/2012 | |
| WO | 2012158957 A2 | 11/2012 | |
| WO | 2013039985 A2 | 3/2013 | |
| WO | 2013049591 A2 | 4/2013 | |
| WO | 2013101830 A1 | 7/2013 | |
| WO | 2013111108 A1 | 8/2013 | |
| WO | 2014145986 A1 | 9/2014 | |
| WO | 2014149139 A2 | 9/2014 | |

OTHER PUBLICATIONS

U.S. Appl. No. 13/630,201, filed Sep. 28, 2012.
U.S. Appl. No. 14/989,742, filed Jan. 6, 2016.
U.S. Appl. No. 15/004,789, filed Jan. 22, 2016.
U.S. Appl. No. 15/155,954, filed May 16, 2016.
U.S. Appl. No. 14/776,612, filed Sep. 14, 2015.
U.S. Appl. No. 15/156,154, filed May 16, 2016.
Albers et al., "Ximelagatran vs warfarin for stroke prevention in patients with nonvalvular atrial fibrillation: a randomized trial," JAMA 293(6):690-8, Feb. 2005.
Calabresi et al., "Section IX Chemotherapy of Neoplastic Diseases Introduction," Goodman & Gilman's the Pharmacological Basis of Therapeutics Tenth Edition: 1381-1388, 2001.
Connolly et al., "Dabigatran versus warfarin in patients with atrial fibrillation," New England Journal of Medicine 361 (12):1139-51, Sep. 17, 2009.
Eriksson et al., "A Dose-ranging Study of the Oral Direct Thrombin Inhibitor, Ximelagatran, and Its Subcutaneous Form, Melagatran, Compared with Dalteparin in the Prophylaxis of Thromboembolism after Hip or Knee Replacement: Methro I," Thrombosis and Haemostasis 87(2):231-237, Feb. 2002.
Eriksson et al., "Dabigatran etexilate versus enoxaparin for prevention of venous thromboembolism after total hip replacement: a randomised, double-blind, non-inferiority trial," The Lancet 370(9591):949-56, Sep. 21, 2007.
Eriksson et al., "Oral dabigatran etexilate vs. subcutaneous enoxaparin for the prevention of venous thromboembolism after total knee replacement: the Re-Model randomized trial," Journal of Thrombosis and Haemostasis 5(11):2178-85, Nov. 1, 2007.
Eriksson et al., "Oral dabigatran versus enoxaparin for thromboprophylaxis after primary total hip arthroplasty (Re-Novate II)," Thrombosis and Haemostasis 105(4):721-729, Apr. 2011.
Eriksson et al., "The direct thrombin inhibitor melagatran followed by oral ximelagatran compared with enoxaparin or the prevention of venous thromboembolism after total hip or knee replacement: the Express study," Journal of Thrombosis and Haemostasis, 1(12):2490-6, Dec. 1, 2003.
Fiessinger et al., "Ximelagatran vs low-molecular-weight heparin and warfarin for the treatment of deep vein hrombosis: a randomized trial," JAMA 293(6):681-9, Feb. 9, 2005.
Francis et al., "Comparison of ximelagatran with warfarin for the prevention of venous thromboembolism after total knee replacement," New England Journal of Medicine, 349(18):1703-12, Oct. 30, 2003.
Ginsberg et al., "Oral Thrombin Inhibitor Dabigatran Etexilate vs North American Enoxaparin Regimen for Prevention of Venous Thromboembolism After Knee Arthroplasty Surgery," The Journal of Arthroplasty 24(1):1-9, Jan. 2009.
Lehman et al., "Bivalirudin in percutaneous coronary intervention," Vascular Health and Risk Management 2(4):357-363, Dec. 2006.
Schmidt et al., "Thrombin Inhibitors Reduce Intrapulmonary Accumulation of Fibrinogen and Procoagulant Activity of Bronchoalveolar Lavage Fluid During Acute Lung Injury Induced by Pulmonary Overdistention in Newborn Piglets1," Pediatnc Research 39(5):798-804, May 1, 1996.
Schulman et al., "Dabigatran versus warfarin in the treatment of acute venous thromboembolism," New England Journal of Medicine 361(24):2342-52, Dec. 10, 2009.
Weitz et al., "Direct Thrombin Inhibitors in Acute Coronary Syndromes: Present and Future," Circulation 105(8):1004-1011, Feb. 26, 2002.
Wåhlander et al., "Pharmacokinetics, pharmacodynamics and clinical effects of the oral direct thrombin inhibitor (xmelagatran in acute treatment of patients with pulmonary embolism and deep vein thrombosis," Thrombosis Research 107(3-4):93-99, Aug. 15, 2002.
Galanud et al., "The history and historical treatments of deep vein thrombosis," Journal of Thrombosis and Heamostasis 11(3):402-411, Mar. 13, 2013.
Kaiser et al., "Synthetic and recombinant antithrombin drugs," Expert Opinion on Investigational Drugs 7(6):963-985, Jun. 1, 1998.
Wolfram et al., "Update on Pharmacologic Approaches to Prevent Thromboembolism in Atrial Fibrillation: Are Thrombin and Factor Xa Inhibitors the Ultimate Answer?," Current Vascular Pharmacology 9(3):350-357, May 2011.
Varnes et al., "Design, structure-activity relationship, and pharmacokinetic profile of pyrazole-based indoline factor Xa inhibitors," Bioorganic & Medicinal Chemistry Letters 17(1):6481-6488, available online Oct. 1, 2007, print publication Dec. 2007.
Varnes et al., "Structure-activity relationship and pharmacokinetic profile of 5-ketopyrazole factor Xa inhibitors," Bioorganic & Medicinal Chemistry Letters 18(2):749-754, available online Nov. 17, 2007, print publication Jan. 15, 2008.
Becker et al., "Why Do So Many Drugs for Alzheimer's Disease Fail in Development? Time for New Methods and New Practices?" Journal of Alzheimer's Disease 15(2):303-325, Oct. 2008.

(56) References Cited

OTHER PUBLICATIONS

Gasparini et al., "Peripheral markers in testing pathophysiological hypotheses and diagnosing Alzheimer's disease," The FASEB Journal 12(1):17-34, Jan. 1998.
Greicius et al., "Presenile dementia syndromes: an update on taxonomy and diagnosis," Journal of Neurology, Neurosurgery, and Psychiatry 72(6):691-700, Jun. 2002.
Mehta et al., "An update on recent patents on thrombin inhibitors (2010-2013)," Expert Opinion on Therapeutic Patents 24(1):47-67, published online Oct. 8, 2013, print publication Jan. 1, 2014.
Schmitt et al., "The kallikreins: old proteases with new clinical potentials," Thrombosis and Haemostasis, 110(3):396-398, Sep. 1, 2013.
Inaba et al., "Suppression of experimental autoimmune encephalomyelitis by dermatan sulfate," Cellular Immunology, 198(2). pp. 96-102. Dec. 15, 1999.
Kakkar et al., "Low Molecular Weight Heparin, Therapy With Dalteparin, and Survival in Advanced Cancer. The Fragmin Advanced Malignancy Outcome Study (FAMOUS)," Journal of Clinical Oncology, 22(10). pp. 1944-1948. May 15, 2004.
Kantlehner et al., "Orthoamide, XXXII. Umsetzungen von tert-Butoxy-N,N,N',N'-tetramethylmethandiamin mit NH-und CH-aciden Verbindungen," Liebigs Annalen der Chemie, 1980(3). pp. 344-357. Mar. 1980.
Katritzky et al. "Selective Reactivity of sp3 and sp2 Carbanions of 1-Substituted 1,2,4-Triazoles. A Comparative Approach," Journal of Organic Chemsitry, 63(13). pp. 4323-4331. Jun. 5, 1998.
Klerk et al., "The Effect of Low Molecular Weight Heparin on Survival in Patients With Advanced Malignancy," Journal of Clinical Oncology, 23(10). pp. 2130-2135. Apr. 1, 2005.
Kranjc et al., "Dual Inhibitors of the Blood Coagulation Enzymes" Current Medicinal Chemistry, 11(19). pp. 2535-2547. Oct. 2004.
Kumar et al., "Efficient Routes to Pyrazolo[3,4-b]indoles and Pyrazolo[1,5-a]benzimidazoles via Palladium- and Copper-Catalyzed Intramolecular C-C and C-N Bond Formation", The Journal of Organic Chemistry, 74(18). pp. 7046-7051. Sep. 18, 2009. Published ahead of print Aug. 11, 2009.
Labanauskas et al., "Synthesis of 3-(3,4-Dimethoxyphenyl)-1H-1,2,4,-Triazole-5-Thiol and 2-Amino-5-(3,4-Dimethoxypheny)-1,3,4-Thiadiazole Derivatives Exhibiting Anti-Inflammatory Activity," Die Pharmazie, 56(8). pp. 317-619. Aug. 2001.
Langer et al., "New methods of drug delivery," Science, 249(4976). pp. 1527-1533. Sep. 28, 1990.
Lee et al., "Randomized comparison of low molecular weight heparin and coumarin derivatives on the survival of patients with cancer and venous thromboembolism," Journal of Clinical Oncology, 23(10). pp. 2123-2129. Apr. 1, 2005.
Lloyd et al., "Benzopyran sulfonamides as Kv1.5 potassium channel blockers," Bioorganic & Medicinal Chemistry Letters, 17(12). pp. 3271-3275. Jun. 15, 2007.
Lottenberg et al., "The action of thrombin on peptide p-Nitroanilide substrates: Substrate selectivity and examination of hydrolysis under different reaction condtions," Biochimica et Biophysica Acta (BBA)—Protein Structure and Molecular Enzymology, 742(3). pp. 539-557. Feb. 15, 1983.
Luo et al., "The Role of Thrombin and Thrombin Receptors in the Brain," in Thrombin: Physiology and Disease, XII. Maragoudakis et al. (eds.). pp. 133-159. 2009.
Miller Keane et al., Miller-Keane Encyclopedia & Dictionary of Medicine, Nursing & Allied Health, 5th Ed. pp. 1651 and 1708. O'Toole (ed.). W.B. Saunders, Philadelphia, PA. 1992.
Montoya et al., "Regioselective formation of N-alkyl-3,5-pyrazole derived ligands. A synthetic and computational study," Tetrahedron, 61(52). pp. 12377-12385. Dec. 26, 2005.
Narita et al., "Protease-activated receptor-1 and platelet-derived growth factor in spinal cord neurons are implicated in neuropathic pain after nerve injury," The Journal of Neuroscience, 25(43). pp. 10000-10009. Oct. 26, 2005.

Nieman et al., "Oral thrombostatin FM19 inhibits prostate cancer," Thrombosis and Haemostasis, 104(5). pp. 1044-1048. Nov. 2010. Published ahead of print Sep. 30, 2010.
Nieman et al., "Thrombostatin FM compounds: direct thrombin inhibitors—mechanism of action in vitro and in vivo," Journal of Thrombosis and Haemostasis, 6(5). pp. 837-845. May 2008. Published ahead of print Feb. 26, 2008.
Pinto et al., "Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa," Journal of Medicinal Chemistry, 44(4). pp. 566-578. Jan. 24, 2001.
Prezelj et al., "Recent Advances in Serine Protease Inhibitors as Anticoagulant Agents," Current Pharmaceutical Design, 13(3). pp. 287-312. Jan. 2007.
Reiter et al., "On Triazoles. VI. The acylation of 5-amino-1,2,4-triazoles," Journal of Heterocyclic Chemistry, 24(1). pp. 127-142. Jan. 1987.
Roche (ed.), Bioreversible Carriers in Drug Design: Theory and Application. 292 pages. Pergamon Press. 1987.
Saalfrank et al., "Geminale Vinyldiazide, VI. 4,5-Dihydro-1H-tetrazol-5-ylidene aus 3,3-Diazido-2-cyanacrylsäureestem and Hydrazinen, Hydraziden sowie O-substituierten Hydroxylaminen," Chemische Berichte, 122(3). pp. 519-522. Mar. 1989.
Schepetkin et al., "N-Benzoylpyrazoles Are Novel Small-Molecule Inhibitors of Human Neutrophil Elastase," Journal of Medicinal Chemistry, 50(20). pp. 4928-4938. Oct. 4, 2007. Published ahead of print Sep. 12, 2007.
Silver et al., "Dabigatran Etexilate, An Oral Direct Thrombin Inhibitor, Represses Fibrotic Changes in a Murine Model of Pulmonary Fibrosis." American Journal of Respiratory and Critical Care Medicine, 181. p. A6780. 2010.
Smiti et al., "Kondensation von 3-Merkapto-5-phenyl-1,2,4-triazole mit Monochloracetaldehyd," Archiv Der Pharmazie, 320(1). pp. 528-534. Jan. 1, 1987.
Smorenburg et al., "The effects of unfractionated heparin on survival in patients with malignancy—a systematic review," Thrombosis and Haemostasis, 82. pp. 1600-1604. 1999.
Stella, "Prodrugs: An Overview and Definition." Pro-drugs as Novel Drug Delivery Systems, vol. 14, Chapter 1. 115 pages. American Chemical Society. Jun. 1, 1975.
STN International File caplus [Online], AN 2007:157737, DN 147: 385893, SO: Zhumal Organichnoi ta Farmatsevtichnoi Kimii 2006, 4(1), p. 32-37, CAS registration No. RN:882238-17-7, 882238-21-3, 882238-25-7, 382239-13-6, 882239-17-0, 882239-21-6.
STN International File Registry [Online]. CAS registration No. RN: 1189909-54-3, 1007171-70-1, 956442-20-9, 956441-56-8, 956375-74-9, 882239-05-6.
STN International Registry File [Online] May 14, 2008, CAS Registration No. RN 1020709-18-5.
STN International Registry File [online], 1975, CAS Registration No. 5945-72-3.
The National Formulary, 14th Ed. American Pharmaceutical Association. Washington, D.C. pp. 1-5. Jul. 1, 1975.
The National Formulary, 14th Ed. American Pharmaceutical Association. Washington, D.C. pp. 6-19. Jul. 1, 1975.
Van Noorden et al., "Experimental and clinical effects of anticoagulants on cancer progression," Thrombosis Search, 125, Supplment 2. pp. S77-S79. Apr. 2010.
Vaughan et al., "Protease nexin-1, a potent thrombin inhibitor, is reduced around cerebral blood vessels in Alzheimer's disease," Brain Research, 668(1-2). pp. 160-170. Dec. 30, 1994.
Wardakhan et al., "Synthesis of novel pyrazole, coumarin, and pyridazine derivatives evaluated as potential antimicrobial and antifungal agents," Journal of the Chilean Chemical Society, 52(2). pp. 1145-1149. Jun. 2007.
Wiedermann et al., "The anti-inflammatory actions of antithrombin—a review," Acta Medica Austriaca, 29(3). pp. 39-92. Jul. 29, 2002.
Wieland et al., "Approaches in anticoagulation: rationales for target positiong," Current Opinion in Investigational Drugs, 4(3). pp. 264-271. Mar. 2003.

(56) References Cited

OTHER PUBLICATIONS

Wong et al., "Nonpeptide Factor Xa Inhibitors III: Effects of DPC423, an Orally-Active Pyrazole Antithrombotic Agent, on Arterial Thrombosis in Rabbits." The Journal of Pharmacolor and Experimental Therapeutics, 303(3). pp. 993-1000. Dec. 1, 2002.
Yin et al., "Brain endothelial cells synthesize neurotoxic thrombin in Alzheimer's disease.," The American Journal of Pathology, 176(4). pp. 1600-1606. Apr. 2010.
Young et al., "Selective and dual action orally active inhibitors of thrombin and factor Xa" Bioorganic & Medicinal Chemistry Letters, 17(10). pp. 2927-2930. May 15, 2007.
Yu et al., "Synthesis and biological activities of 5-substituted benzamide triazole," Journal of Central China Normal University, Natural Sciences Edition, 37(4). pp. 505-503. 2003. Accessed from Database CAPLUS. Database accession No. 2004:240714.
Zacharski et al., "Heparin as an anticancer therapeutic," Expert Opinion on Investigational Drugs, 17(7). pp. 1029-1037. Jun. 12, 2008.
Bader, "Kallikrein-Kinin System in Neovascularization," Arteriosclerosis, Thombosis, and Vascular Biology, 29(5). pp. 617-619. May 2009.
Caliendo et al., "Kallikrein Protease Activated Receptor (PAR) Axis: An Attractive Target for Drug Development," Journal of Medicinal Chemistry, 55(15). pp. 6669-6686. May 18, 2012.
Feener et al., "Plasma Kallikrein and Diabetic Macular Edema," Current Diabetes Reports, 10(4). pp. 270-275. Published ahead of print, Jun. 10, 2010.
Hallet, "Acute Peripheral Arterial Occulusion," Merck Manual, Professional/Cardiovascular Disorders/Peripheral Arterial Disorders, two pages, May, 2014.
Heit et al., "Comparison of the Oral Direct Thrombin Inhibitor Ximelagatran With Enoxaparin as Prophylaxis Against Venous Thromboembolism After Total Knee Replacement: A Phase 2 Dose-Finding Study," Archives of Internal Medicine 161(18): 2215-2221, Oct. 8, 2001.
International Search Report and Written Opinion in International Patent Application No. PCT/US2014/030853. dated Jul. 17, 2014. Published Sep. 18, 2014. 12 pages.
Kokolis et al., "Anticoagulation strategies for patients undergoing percutaneous coronary intervention: unfractionated heparin, low-molecular-weight heparins, and direct thrombin inhibitors." Progress in Cardiovascular Disease, 46 (6):506-523. May-Jun. 2004.
Miura "Transactivation of KDR/Flk-1 by the B2 receptor induces tube formation in human coronary endothelial cells," Hypertension, 41(5). pp. 1118-1123. Published ahead of print Mar. 24, 2003.
Moreau et al., "The kallikrein-kinin system: current and future pharmacological targets," Journal of Pharmacological Sciences, 99(1). pp. 6-38. Sep. 22, 2005.
Official Action in Russian Patent Application No. 2012146194. dated Mar. 29, 2016. 4 pages.
Renné, "Plasma kallikrein: Novel functions for an old protease," Thrombosis and Haemostasis, 107(6). pp. 1012-1013. Jun. 2012.
Robertson et al., "Oral direct thrombin inhibitors or oral factor Xa inhibitors for the treatment of deep vein thrombosis." The Cochrane Database of Systemic Reviews, 6:CD010956. Jun. 30, 2015.
Schneider et al., "Critical role of kallikrein in hereditary angioedema pathogenesis: a clinical trial of ecallantide, a novel kallikrein inhibitor," Journal of Allergy and Clinical Immunology, 120(2). pp. 416-422. Aug. 2007.
Sotiropoulou et al., "Targeting the kallikrein-related peptidases for drug development," .Trends in Pharmacological Sciences, 33(12). pp. 623-634. Dec. 2012.
Syed et al., "Wet AMD market," Nature Reviews Drug Discovery, 11. pp. 827-828. Nov. 2012.
Xiong et al., "Discovery and Structure-Activity Relationship of 3-Methoxy- N -(3-(1-methyl-1 H -pyrazol -5-y-l)-4-(2-morpholinoethoxy)phenyilbenzamide (APD791): A Highly Selective 5-Hydroxytryptamine 2A Receptor Inverse Agonist for the Treatment of Arterial Thrombosis," Journal of Medicinal Chemistry 53(11):4412-4421, Jun. 10, 2010, ISSN: 0022-2623, DOI: 10.1021/jm100044a.
Diener et al., "Stroke prevention using the oral direct thrombin inhibitor ximelagatran in patients with non-valvular atrial fibrillation. Pooled analysis from the SPORTIF III and V studies." Cerebrovascular Diseases, 21(4):279-293. Mar. 2006.
Eriksson et al., "Direct thrombin inhibitor melagatran followed by oral ximelagatran in comparison with enoxaparin for prevention of venous thromboembolism after total hip or knee replacement." Thrombosis and Haemostasis, 89(2):288-296. Feb. 2003.
Extended European Search Report dated Aug. 28, 2013, European Patent Application No. 11766507.5, filed Mar. 30, 2011.
Francis et al., "Ximelagatran versus warfarin for the prevention of venous thromboembolism after total knee arthroplasty. A randomized, double-blind trial." Annals of Internal Medicine, 137(8):648-655. Oct. 15, 2002.
Freitas et al., "Isomannide derivatives as new class of inhibitors for human kallikrein 7," Bioorganic & Medicinal chemistry Letters, 22(19). pp. 6072-6075. Oct. 1, 2012.
Hankey et al, "Antithrombotic Drugs for Patients with Ischaemic Stroke and Transient Ischaemic Attack to Prevent Recurrent Major Vascular Events," The Lancet Neurology, 9(3):273-284, Mar. 2010.
Keel et al., "Pathophysiology of polytrauma," Injury, 36(6). pp. 691-709. Jun. 2005.
Lewis et al., "Argatroban anticoagulation during percutaneous coronary intervention in patients with heparin-induced thrombocytopenia." Catheterization & Cardiovascular Interventions, 57(2)177-184. Oct. 2002. Published ahead of print Sep. 30, 2002.
Olsson et al., "Stroke prevention with the oral direct thrombin inhibitor ximelagatran compared with warfarin in patients with non-valvular atrial fibrillation (SPORTIF III): randomised controlled trial.," Lancet, 362(9397): 1691-1698, Nov. 22, 2003.
Telander, "Inflammation and age-related macular degeneration (AMD)," Seminars in Ophthalmology, 26(3). pp. 192-197. Published online May 24, 2011.
Bird et al., "Effects of plasma kallikrein deficiency on haemostasis and thrombosis in mice: Murine Ortholog of the Fletcher Trait," Thrombosis and Haemostasis, 107(6). pp. 1141-1150. Jun. 2012.
Eriksson et al., "Direct thrombin inhibitor melagatran followed by oral ximelagatran in comparison with enoxaparin or prevention of venous thromboembolism after total hip or knee replacement." Thrombosis and Haemostasis, 89(2):288-296. Feb. 2003.
Freitas et al., "Isomannide derivatives as new class of inhibitors for human kallikrein 7," Bioorganic & Medicinal Chemistry Letters, 22(19). pp. 6072-6075. Oct. 1, 2012.
International Search Report and Written Opinion dated Jul. 17, 2014, International Patent Application No. PCT/US2014/030853, filed Mar. 17, 2014.
Lewis et al., "Argatroban anticoagulation during percutaneous coronary intervention in patients with heparin-induced thrombocytopenia." Catheterization & Cardiovascular Interventions, 57(2):177-184. Oct. 2002. Published ahead of print Sep. 30, 2002.
Ramalakshmi et al., "Synthesis, Characterization and Biological Screening of Some Novel 1,3,5 Trisubstituted 2-Pyrazolines," Rasayan Journal of Chemistry 2(2):393-396, Apr. 2009.
Albert-Weiβenberger et al., "Ischemic stroke and traumatic brain injury: The role of the kallikrein-kinin system," Progress in Neurobiology 101-102:65-82, Feb.-Mar. 2013.
Colman et al., "The plasma kallikrein-kinin system in sepsis, inflammatory arthritis, and enterocolitis," Clinical Reviews in Allergy and Immunology 16(4):365-384, Dec. 1998.
Feener et al., "Plasma Kallikrein Kinin System and Diabetic Retinopathy," Biological Chemistry 394(3):319-328, published online Feb. 2, 2013, print publication Mar. 1, 2013.
Ferrrera, "VEGF: an update on biological and therapeutic aspects," Current Opinion in Biotechnology 11(6):617-624, Dec. 1, 2000.
Kolte et al., "PF-04886847 (an Inhibitor of Plasma Kallikrein) Attenuates Inflammatory Mediators and Activation of Blood Coagulation in Rat Model of Lipopolysaccharide (LPS)—Induced

(56) References Cited

OTHER PUBLICATIONS

Sepsis," Cardiovascular & Hematological Agents in Medicinal Chemistry 10(2):154-66, Feb. 2012.
Kraut, "Serine Proteases: Structure and Mechanism of Catalysis," Annual Review of Biochemistry 46(1):331-358, Jul. 1977.
Lopez et al., "Transdifferentiated retinal pigment epithelial cells are immunoreactive for vascular endothelial growth factor in surgically excised age-related macular degeneration-related choroidal neovascular membranes," Investigative Ophthalmology & Visual Science 37(5):855-868, Apr. 1996.
U.S. Appl. No. 15/605,566, filed May 25, 2017.
U.S. Appl. No. 15/512,037, filed Mar. 16, 2017.
"Medication Guide: Pradaxa (pra dax' a) (dabigatran etexilate mesylate) capsules," Boehringer Ingelheim Pharmaceuticals, Inc., copyright 2010, FDA approval Sep. 20, 2010, four pages.
Beilin et al., "Increased Thrombin Inhibition in Experimental Autoimmune Encephalomyelitis," Journal of Neuroscience Research 79(3):351-359, published online Dec. 16, 2004, print publication Feb. 1, 2005.
Brown, "A New Era of Anticoagulation: Factor Xa and Direct Thrombin Inhibitors," U.S. Pharmacist 32(3):HS-35-HS-48, Mar. 21, 2007, 25 pages.

\* cited by examiner

HALOGENOPYRAZOLES AS INHIBITORS OF THROMBIN

CROSS-REFERENCE TO RELATED APPLICATIONS

The present application is a U.S. National Stage entry under 35 U.S.C. § 371 of International Application No. PCT/US2014/000058, filed on Mar. 17, 2014, designating the United States of America and published in English on Sep. 25, 2014, which in turn claims priority to U.S. Provisional Application No. 61/789,358, filed on Mar. 15, 2013 and U.S. Provisional Application No. 61/899,588 filed on Nov. 4, 2013, each of which is hereby incorporated by reference in its entirety.

BACKGROUND OF THE INVENTION

The present disclosure relates to compounds, e.g., multi-substituted aromatic compounds, which exhibit biological activity, e.g., inhibitory action, against thrombin (activated blood-coagulation factor II; EC 3.4.21.5).

In mammalian systems, blood vessel injuries result in bleeding events, which are dealt with by the blood coagulation cascade. The cascade includes the Extrinsic and Intrinsic pathways, involving the activation of at least 13 interconnected factors and a variety of co-factors and other regulatory proteins. Upon vascular injury, plasma factor VII interacts with exposed Tissue Factor (TF), and the resultant TF-fVIIa complex initiates a complex series of events. Factor fXa is produced directly 'downstream' from the TF-fVIIa complex, and amplified manifold via the Intrinsic Pathway. FXa then serves as the catalyst for formation of thrombin (fIIa), which in turn is the direct precursor to fibrinolysis. The outcome is a fibrinolytic clot, which stops the bleeding. Fibrinolysis of the polymeric clot into fibrin monomers leads to dissolution and a return of the system to the pre-clot state. The cascade is a complex balance of factors and co-factors and is tightly regulated.

In disease states, undesired up- or down-regulation of any factor leads to conditions such as bleeding or thrombosis. Historically, anticoagulants have been used in patients at risk of suffering from thrombotic complications, such as angina, stroke and heart attack.

Warfarin has enjoyed dominance as a first-in-line anticoagulant therapeutic. Developed in the 1940s, it is a Vitamin K antagonist and inhibits factors II, VII, IX and X, amongst others. It is administered orally, but its ease of use is tempered by other effects: it has a very long half life (>2 days) and has serious drug-drug interactions. Importantly, since Vitamin K is a ubiquitous cofactor within the coagulation cascade, antagonism results in the simultaneous inhibition of many clotting factors and thus can lead to significant bleeding complications.

Much attention has been focused on heparin, the naturally-occurring polysaccharide that activates AT III, the endogenous inhibitor of many of the factors in the coagulation cascade. The need for parenteral administration for the heparin-derived therapeutics, and the inconvenient requirements for close supervision for the orally available warfarin, has resulted in a drive to discover and develop orally available drugs with wide therapeutic windows for safety and efficacy.

Indeed, the position of thrombin in the coagulation cascade has made it a popular target for drug discovery. Without wishing to be bound by any theory, it is believed that the ultimate development of direct thrombin inhibitors (DTIs) is usefully based upon the classical D-Phe-Pro-Arg motif, a sequence that mimics fibrinogen, which is a natural substrate of thrombin. Without further wishing to be bound by any theory, it is believed that the use of DTIs is very well precedented, such as with the hirudin-based anticoagulants, and thus there is strong interest in the discovery and development of novel DTIs.

A thorough discussion of thrombin and its roles in the coagulation process can be found in a variety of references, including the following which are incorporated herein by reference in their entireties and for all purposes: Wieland, H. A., et al., 2003, *Curr Opin Investig Drugs*, 4:264-71; Gross, P. L. & Weitz, J. I., 2008, *Arterioscler Thromb Vasc Biol*, 28:380-6; Hirsh, J., et al., 2005, *Blood*, 105:453-63; Prezelj, A., et al., 2007, *Curr Pharm Des*, 13:287-312.

BRIEF SUMMARY OF THE INVENTION

Embodiments of the invention encompass compounds with structure of Formula (Ia):

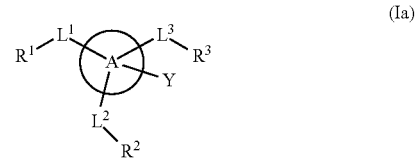

(Ia)

or pharmaceutically acceptable salt, ester, solvate, or prodrug thereof; wherein Ring A can be substituted or unsubstituted pyrazolyl; $L^1$ and $L^3$ can be independently a bond, substituted or unsubstituted alkylene, substituted or unsubstituted heteroalkylene, —S—, —SO—, —SO$_2$—, —O—, —NHSO$_2$—, or —NR$^4$—; $L^2$ can be absent, a bond, substituted or unsubstituted alkylene, substituted or unsubstituted eteroalkylene, —S—, —SO—, —SO$_2$—, —O—, —NHSO$_2$—, or —NR$^4$—; $R^1$ and $R^3$ can be independently hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl; $R^2$ can be absent, hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl, provided that when $L^2$ can be absent, $R^2$ can be absent; $R^4$ can be hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, and substituted or unsubstituted fused ring aryl or substituted or unsubstituted heteroaryl; and Y can be a halogen. In some embodiments of the methods, $L^2$ and $R^2$ can be absent. In some embodiments, the compound can have the structure of Formula (IIa) or Formula (IIb):

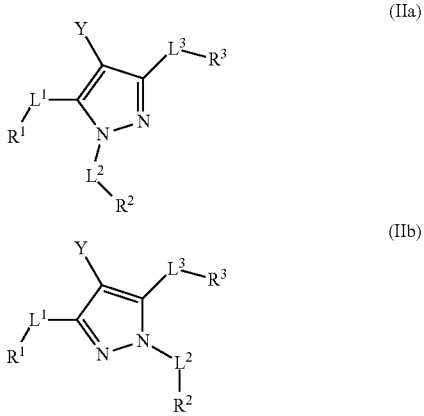

In some embodiments where the compound can have the structure of Formula (IIa), $L^3$ can be a bond, or substituted or unsubstituted alkylene, and $R^3$ can be substituted or unsubstituted aryl, substituted or unsubstituted fused ring aryl, substituted or unsubstituted heterocycloalkyl, or substituted or unsubstituted heteroaryl, and Y can be fluorine. In some embodiments where the compound can have the structure of Formula (IIa), $L^3$ can be —C(O)O—, $R^3$ can be substituted or unsubstituted alkyl, and Y can be fluorine. In some embodiments where the compound can have the structure of Formula (IIa), $L^3$ can be —C(O)NR$^5$—, $R^5$ can be hydrogen or alkyl, $R^3$ can be substituted or unsubstituted alkyl, or substituted or unsubstituted aryl, and Y can be fluorine. In some embodiments, $R^3$ can be substituted or unsubstituted phenyl. In some embodiments, the heteroaryl can be pyridyl, pyridazinyl, pyrimidinyl, thienyl, or furyl. In some embodiments, $R^3$ can be chloro-substituted thienyl. In some embodiments, the heterocycloalkyl can be morpholinyl, oxanyl, or oxetanyl. In some embodiments, the fused ring aryl can be benzodioxinyl or naphthyl. In some embodiments, L' can be a bond, —S—, —NR$^4$—, substituted or unsubstituted alkylene, or substituted or unsubstituted heteroalkylene, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^1$ can be chloro-substituted thienyl. In some embodiments, the heterocycloalkyl can be morpholinyl, oxanyl, or oxetanyl. In some embodiments, the fused ring aryl can be benzodioxinyl or naphthyl. In some embodiments, $R^1$ can be substituted or unsubstituted phenyl. In some embodiments, $L^2$ can be a bond, and $R^2$ can be hydrogen. In some embodiments, $L^2$ can be substituted or unsubstituted alkylene or —C(O)—, and $R^2$ can be hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, the heteroaryl can be pyridyl, pyridazinyl, pyrimidinyl, thienyl, or furyl. In some embodiments, $R^2$ can be substituted or unsubstituted alkyl, substituted or unsubstituted cycloalkyl, or substituted or unsubstituted heterocycloalkyl. In some embodiments, the heterocycloalkyl can be morpholinyl, oxanyl, or oxetanyl. In some embodiments, the fused ring aryl can be benzodioxinyl or naphthyl. In some embodiments, $R^2$ can be substituted or unsubstituted phenyl.

In some embodiments where the compound can have the structure of Formula (IIb), $L^3$ can be a bond, or substituted or unsubstituted alkylene, $R^3$ can be substituted or unsubstituted aryl, substituted or unsubstituted fused ring aryl, substituted or unsubstituted heterocycloalkyl, or substituted or unsubstituted heteroaryl, and Y can be fluorine. In some embodiments where the compound can have the structure of Formula (IIa), $L^3$ can be —C(O)O—, $R^3$ can be substituted or unsubstituted alkyl, and Y can be fluorine. In some embodiments where the compound can have the structure of Formula (IIa), $L^3$ can be —C(O)NR$^5$—, $R^5$ can be hydrogen or alkyl, $R^3$ can be substituted or unsubstituted alkyl, or substituted or unsubstituted aryl, and Y can be fluorine. In some embodiments, $R^3$ can be substituted or unsubstituted phenyl. In some embodiments, the heteroaryl can be pyridyl, pyridazinyl, pyrimidinyl, thienyl, or furyl. In some embodiments, $R^3$ can be chloro-substituted thienyl. In some embodiments, the heterocycloalkyl can be morpholinyl, oxanyl, or oxetanyl. In some embodiments, the fused ring aryl can be benzodioxinyl or naphthyl. In some embodiments, L' can be a bond, —S—, —NR$^4$—, substituted or unsubstituted alkylene, or substituted or unsubstituted heteroalkylene, and $R^1$ can be hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, the heteroaryl can be pyridyl, pyridazinyl, pyrimidinyl, thienyl, or furyl. In some embodiments, $R^1$ can be chloro-substituted thienyl. In some embodiments, the heterocycloalkyl can be morpholinyl, oxanyl, or oxetanyl. In some embodiments, the fused ring aryl can be benzodioxinyl or naphthyl. In some embodiments, $R^1$ can be substituted or unsubstituted phenyl. In some embodiments, $L^2$ can be a bond, and $R^2$ can be hydrogen. In some embodiments, $L^2$ can be substituted or unsubstituted alkylene or —C(O)—, and $R^2$ can be hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, the heteroaryl can be pyridyl, pyridazinyl, pyrimidinyl, thienyl, or furyl. In some embodiments, $R^2$ can be substituted or unsubstituted alkyl, substituted or unsubstituted cycloalkyl, or substituted or unsubstituted heterocycloalkyl. In some embodiments, the heterocycloalkyl can be morpholinyl, oxanyl, or oxetanyl. In some embodiments, the fused ring aryl can be benzodioxinyl or naphthyl. In some embodiments, $R^2$ can be substituted or unsubstituted phenyl. In some embodiments, the compound can be selected from those set forth in Table A.

Embodiments of the invention also encompass pharmaceutical compositions including such compounds, or a compound as set forth in Table A, and a pharmaceutically acceptable excipient. Embodiments of the invention also encompass methods for treating a disease or disorder in a subject, including administering such compounds or pharmaceutical compositions to a subject in need thereof in an amount effective to treat said disease or disorder. In some embodiments, the disease or disorder is a thrombotic disorder. In some embodiments, the thrombotic disorder is acute coronary syndrome, venous thromboembolism, arterial thromboembolism or cardiogenic thromboembolism. In some embodiments, the disease or disorder is fibrosis. In some embodiments, the disease or disorder is Alzheimer's Disease. In some embodiments, the disease or disorder is multiple sclerosis. In some embodiments, the disease or disorder is pain. In some embodiments, the disease or disorder is cancer. Embodiments of the invention also encompass methods for preventing a disease or disorder in a subject, including administering such compounds or pharmaceutical compositions to a subject in need thereof in an amount effective to prevent said disease or disorder. In some embodiments, the disease or disorder can be a thrombotic disorder. In some embodiments, the thrombotic disorder can be acute coronary syndrome, venous thromboembolism, arterial thromboembolism or cardiogenic thromboembolism. In some embodiments, the thrombotic disorder can be disseminated intravascular coagulation. In some embodiments, the thrombotic disorder involves the presence or the potential formation of a blood clot thrombus.

BRIEF DESCRIPTION OF THE DRAWINGS

Not applicable.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "attached" signifies a stable covalent bond, certain preferred points of attachment being apparent to those of ordinary skill in the art.

The terms "halogen" or "halo" include fluorine, chlorine, bromine, and iodine. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "alkyl," by itself or as part of another substituent, means, unless otherwise stated, a straight (i.e., unbranched) or branched chain, or combination thereof, which can be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Accordingly, the term "alkyl" can refer to C$_1$-C$_{16}$ straight chain saturated, C$_1$-C$_{16}$ branched saturated, C$_3$-C$_8$ cyclic saturated and C$_1$-C$_{16}$ straight chain or branched saturated aliphatic hydrocarbon groups substituted with C$_3$-C$_8$ cyclic saturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopropylmethyl, and the like.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the compounds disclosed herein. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms can optionally be oxidized, and the nitrogen heteroatom can optionally be quaternized. The heteroatom(s) O, N, P, S, and Si can be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms can be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "alkenyl" includes $C_2$-$C_{16}$ straight chain unsaturated, $C_2$-$C_{11}$ branched unsaturated, $C_5$-$C_8$ unsaturated cyclic, and $C_2$-$C_{16}$ straight chain or branched unsaturated aliphatic hydrocarbon groups substituted with $C_3$-$C_8$ cyclic saturated and unsaturated aliphatic hydrocarbon groups having the specified number of carbon atoms. Double bonds can occur in any stable point along the chain and the carbon-carbon double bonds can have either the cis or trans configuration. For example, this definition shall include but is not limited to ethenyl, propenyl, butenyl, pentenyl, hexenyl, heptenyl, octenyl, nonenyl, decenyl, undecenyl, 1,5-octadienyl, 1,4,7-nonatrienyl, cyclopentenyl, cyclohexenyl, cycloheptenyl, cyclooctenyl, ethylcyclohexenyl, butenylcyclopentyl, 1-pentenyl-3-cyclohexenyl, and the like. Similarly, "heteroalkenyl" refers to heteroalkyl having one or more double bonds.

The term "alkynyl" refers in the customary sense to alkyl additionally having one or more triple bonds. The term "cycloalkenyl" refers to cycloalkyl additionally having one or more double bonds. The term "heterocycloalkenyl" refers to heterocycloalkyl additionally having one or more double bonds.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Each of the above terms (e.g., "alkyl," "heteroalkyl," "aryl," and "heteroaryl") includes both substituted and unsubstituted forms of the indicated radical. Preferred substituents for each type of radical are provided herein.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound disclosed herein includes more than one R group, for example, each of the R groups is independently selected as are each R', R", and R'" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", and R'" groups when more than one of these groups is present.

Two or more substituents can optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring can optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed can optionally be replaced with a double bond. Alternatively, two of the substituents on adjacent atoms of the aryl or heteroaryl ring can optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

The term "alkyloxy" (e.g. methoxy, ethoxy, propyloxy, allyloxy, cyclohexyloxy) represents an alkyl group as defined above having the indicated number of carbon atoms attached through an oxygen bridge (—O—).

The term "alkylthio" (e.g. methylthio, ethylthio, propylthio, cyclohexylthio and the like) represents an alkyl group as defined above having the indicated number of carbon atoms attached through a sulfur bridge (—S—).

The term "alkylamino" represents one or two alkyl groups as defined above having the indicated number of carbon atoms attached through an amine bridge. The two alkyl groups can be taken together with the nitrogen to which they are attached forming a cyclic system containing 3 to 8 carbon atoms with or without one $C_1$-$C_{16}$alkyl, aryl$C_0$-$C_{16}$alkyl, or $C_0$-$C_{16}$alkylaryl substituent.

The term "alkylaminoalkyl" represents an alkylamino group attached through an alkyl group as defined above having the indicated number of carbon atoms.

The term "alkyloxy(alkyl)amino" (e.g. methoxy(methyl) amine, ethoxy(propyl)amine) represents an alkyloxy group as defined above attached through an amino group, the amino group itself having an alkyl substituent.

The term "alkylcarbonyl" (e.g. cyclooctylcarbonyl, pentylcarbonyl, 3-hexylcarbonyl) represents an alkyl group as defined above having the indicated number of carbon atoms attached through a carbonyl group.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen.

The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonylaminomethyl, methylcarbonylaminophenyl) represents an alkylcarbonyl group as defined above wherein the carbonyl is in turn attached through the nitrogen atom of an amino group.

The nitrogen group can itself be substituted with an alkyl or aryl group.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Accordingly, the term "aryl" can represent an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g. 3-indolyl, 4-imidazolyl). The aryl substituents are independently selected from the group consisting of halo, nitro, cyano, trihalomethyl, $C_{1-16}$alkyl, aryl$C_{116}$alkyl, $C_{0-16}$alkyloxy$C_{0-16}$alkyl, aryl$C_{0-16}$alkyloxy$C_{0-16}$alkyl, $C_{0-16}$alkylthio$C_{0-16}$alkyl, aryl$C_{0-16}$alkylthio$C_{0-16}$alkyl, $C_{0-16}$alkylamino$C_{0-16}$alkyl, aryl$C_{0-16}$alkylamino$C_{0-16}$alkyl, di(aryl$C_{1-16}$alkyl)amino$C_{0-16}$alkyl, $C_{1-16}$alkylcarbonyl$C_{0-16}$alkyl, aryl$C_{1-16}$alkylcarbonyl$C_{0-16}$alkyl, $C_{1-16}$alkylcarboxy$C_{0-16}$alkyl, aryl$C_{1-16}$alkylcarboxy$C_{0-16}$alkyl, $C_{1-16}$alkylcarbonylamino$C_{0-16}$alkyl, aryl$C_{1-16}$alkylcarbonylamino$C_{0-16}$alkyl, —$C_{0-16}$alkyl-$COOR_4$, —$C_{0-16}$alkyl$CONR_5R_6$ wherein $R_4$, $R_5$ and $R_6$ are independently selected from hydrogen, $C_{1-11}$alkyl, aryl$C_0$-$C_{11}$alkyl, or $R_5$ and $R_6$ are taken together with the nitrogen to which they are attached forming a cyclic system containing 3 to 8 carbon atoms with or without one $C_{1-16}$alkyl, aryl$C_0$-$C_{16}$alkyl, or $C_0$-$Cl_{16}$alkylaryl substituent. Aryl includes but is not limited to pyrazolyl and triazolyl.

For brevity, the term "aryl" when used in combination with other terms (e.g., aryloxy, arylthioxy, arylalkyl) includes both aryl and heteroaryl rings as defined above. Thus, the terms "arylalkyl," "aralkyl" and the like are meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like), or a sulfur atom. Accordingly, the terms "arylalkyl" and the like (e.g. (4-hydroxyphenyl)ethyl, (2-aminonaphthyl)hexyl, pyridylcyclopentyl) represents an aryl group as defined above attached through an alkyl group as defined above having the indicated number of carbon atoms.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' can have a specified number of carbons (e.g., "$C_1$-$C_4$ alkylsulfonyl").

The term "carbonyloxy" represents a carbonyl group attached through an oxygen bridge.

In the above definitions, the terms "alkyl" and "alkenyl" can be used interchangeably in so far as a stable chemical entity is formed, as would be apparent to those skilled in the art.

The term "linker" refers to attachment groups interposed between substituents, e.g., $R^1$, $R^2$ or $R^3$ described herein, e.g., Formula (Ia) and generically referred to as R″, and the group which is substituted, e.g., "ring A" group of e.g., Formula (Ia). In some embodiments, the linker includes amido (—CONH—R″ or —NHCO—R″), thioamido (—CSNH—R″ or —NHCS—R″), carboxyl (—CO₂—R″ or —OCOR″), carbonyl (—CO—R″), urea (—NHCONH—R″), thiourea (—NHCSNH—R″), sulfonamido (—NHSO₂—R″ or —SO₂NH—R″), ether (—O—R″), sulfonyl (—SO₂—R″), sulfoxyl (—SO—R″), carbamoyl (—NHCO₂—R″ or —OCONH—R″), or amino (—NHR″) linking moieties.

A "substituent group," as used herein, means a group selected from the following moieties:

(A) —OH, —NH₂, —SH, —CN, —CF₃, —NO₂, oxo, halogen, —COOH, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —NH₂, —SH, —CN, —CF₃, —NO₂, halogen, —COOH, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH₂, —SH, —CN, —CF₃, —NO₂, halogen, —COOH, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH₂, —SH, —CN, —CF₃, —NO₂, halogen, —COOH, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "about" used in the context of a numeric value indicates a range of +/- 10% of the numeric value, unless expressly indicated otherwise.

II. Compounds

In one aspect, there is provided a compound with structure of Formula (Ia):

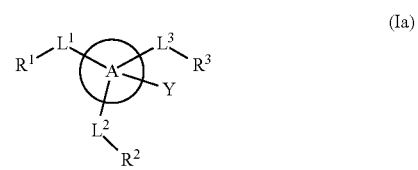

(Ia)

or pharmaceutically acceptable salt, ester, solvate, or prodrug thereof. Ring A is substituted or unsubstituted pyrazolyl. $L^1$ and $L^3$ are independently a bond, substituted or unsubstituted alkylene, substituted or unsubstituted heteroalkylene, —S—, —SO—, —SO₂—, —O—, —NHSO₂—, or –NR⁴—. $L^2$ is absent, a bond, a hydrogen, substituted or unsubstituted alkylene, substituted or unsubstituted heteroalkylene, —S—, —SO—, —SO₂—, —O—, —NHSO₂—, or —NR⁴—. $R^1$ and $R^3$ are independently hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. $R^2$ is absent, hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. $R^4$ is hydrogen, substituted or unsubstituted alkyl, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl. Y is a halogen. In some embodiments, $R^2$ can be absent provided $L^2$ is also absent.

In some embodiments, the compound is a pharmaceutically acceptable salt, ester, solvate, or prodrug of a compound of Formula (Ia). In some embodiments, the compound is not an ester, not a solvate, and not a prodrug.

Further to any embodiment above, in some embodiments $L^1$ is —S—, —NR⁴—, substituted or unsubstituted alkylene, or substituted or unsubstituted heteroalkylene, where $R^4$ is as described above in regards to formula Ia, and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^3$ is substituted or unsubstituted aryl. In some embodiments, $R^3$ is unsubstituted aryl. In some embodiments, $R^3$ is unsubstituted phenyl. In some embodiments, $L^2$ is a bond. In some embodiments, $L^2$ is a bond and $R^2$ is hydrogen. Y is fluorine.

Further to any embodiment above, in some embodiments $L^2$ is —C(O)—, and $R^2$ is substituted or unsubstituted alkyl, hydrogen, substituted or unsubstituted heteroalkyl, substituted or unsubstituted alkylene, substituted or unsubstituted heteroalkylene, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, substituted or unsubstituted fused ring aryl, or substituted or unsubstituted heteroaryl. In some embodiments, $R^2$ is unsubstituted aryl. In some embodiments, $R^2$ is unsubstituted phenyl.

In some embodiments, $L^2$ and $R^2$ are absent, providing a compound with structure of Formula (Ib) following.

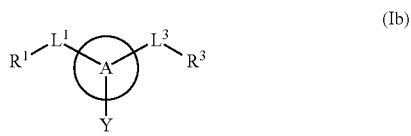

(Ib)

In some embodiments, the compound is a pharmaceutically acceptable salt, ester, solvate, or prodrug of a compound of Formula (Ib). In some embodiments, the compound is not an ester, not a solvate, and not a prodrug.

In some embodiments, there is provided a compound according to Formula (Ia) with structure of either of Formulae (IIa) or (IIb) following.

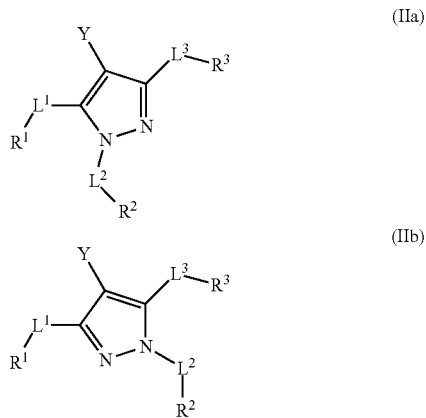

(IIa)

(IIb)

In some embodiments, the compound has the structure of Formula (IIa). In some embodiments, $L^3$ is a bond, or substituted or unsubstituted alkylene, and $R^3$ is substituted or unsubstituted aryl, substituted or unsubstituted fused ring aryl, substituted or unsubstituted heterocycloalkyl, or substituted or unsubstituted heteroaryl. In some embodiments, $R^3$ is substituted or unsubstituted phenyl, or substituted or unsubstituted thienyl. In some embodiments, $R^3$ is unsubstituted phenyl. In some embodiments, $R^3$ is unsubstituted thienyl. In some embodiments, $R^3$ is a chloro-substituted thienyl. In some embodiments, $R^3$ is substituted or unsubstituted pyridyl, or substituted or unsubstituted pyridazinyl. In some embodiments, $R^3$ is unsubstituted pyridyl. In some embodiments, $R^3$ is unsubstituted pyridazinyl. In some embodiments, $R^3$ is substituted or unsubstituted pyrimidinyl, or substituted or unsubstituted furyl. In some embodiments, $R^3$ is unsubstituted pyrimidinyl. In some embodiments, $R^3$ is unsubstituted furyl. In some embodiments, $R^3$ is substituted or unsubstituted morpholinyl, or substituted or unsubstituted oxanyl, or substituted or unsubstituted oxetanyl. In some embodiments, $R^3$ is unsubstituted morpholinyl. In some embodiments, $R^3$ is unsubstituted oxanyl. In some embodiments, $R^3$ is unsubstituted oxetanyl. In some embodiments, $R^3$ is substituted or unsubstituted benzodioxinyl, or substituted or unsubstituted naphthyl. In some embodiments, $R^3$ is unsubstituted benzodioxinyl. In some embodiments, $R^3$ is unsubstituted naphthyl. In some embodiments, $R^3$ is substituted or unsubstituted phenyl. In some embodiments, Y is fluorine.

In some embodiments, the compound has the structure of Formula (IIa) wherein $L^3$ is —C(O)O—, and $R^3$ is substituted or unsubstituted alkyl, and Y is fluorine.

In some embodiments, the compound has the structure of Formula (IIa) wherein $L^3$ is —C(O)NR$^5$—, $R^5$ is hydrogen or alkyl, and $R^3$ is substituted or unsubstituted alkyl and Y is fluorine.

Further to any embodiment above wherein the compound has the structure of Formula (IIa), in some embodiments, $L^1$ is —S—, a bond, —NR$^4$—, substituted or unsubstituted alkylene, or substituted or unsubstituted heteroalkylene, where $R^4$ is as described in formula Ia and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is a substituted or unsubstituted pyridyl. In some embodiments, $R^1$ is a substituted or unsubstituted pyridazinyl. In some embodiments, $R^1$ is a substituted or unsubstituted pyrimidinyl. In some embodiments, $R^1$ is a substituted or unsubstituted thienyl. In some embodiments, $R^1$ is a substituted or unsubstituted furyl. In some embodiments, $R^1$ is an unsubstituted pyridyl. In some embodiments, $R^1$ is an unsubstituted pyridazinyl. In some embodiments, $R^1$ is an unsubstituted pyrimidinyl. In some embodiments, $R^1$ is an unsubstituted thienyl. In some embodiments, $R^1$ is a chloro-substituted thienyl. In some embodiments, $R^1$ is an unsubstituted furyl. In some embodiments, $R^1$ is a substituted or unsubstituted morpholinyl. In some embodiments, $R^1$ is a substituted or unsubstituted oxanyl. In some embodiments, $R^1$ is a substituted or unsubstituted oxetanyl. In some embodiments, $R^1$ is an unsubstituted morpholinyl. In some embodiments, $R^1$ is an unsubstituted oxanyl. In some embodiments, $R^1$ is an unsubstituted oxetanyl. In some embodiments, $R^1$ is substituted or unsubstituted benzodioxinyl. In some embodiments, $R^1$ is substituted or unsubstituted naphthyl. In some embodiments, $R^1$ is unsubstituted benzodioxinyl. In some embodiments, $R^1$ is unsubstituted naphthyl. In some embodiments, $R^1$ is substituted or unsubstituted phenyl. In some embodiments, Y is fluorine.

Further to any embodiment above wherein the compound has the structure of Formula (IIa), in some embodiments, $L^2$ is a bond. In some embodiments, $R^2$ is hydrogen. In some embodiments, $L^2$ is substituted or unsubstituted alkylene or —C(O)—, and $R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ is a substituted or unsubstituted pyridyl. In some embodiments, $R^2$ is a substituted or unsubstituted pyridazinyl. In some embodiments, $R^2$ is a substituted or unsubstituted pyrimidinyl. In some embodiments, $R^2$ is a substituted or unsubstituted thienyl. In some embodiments, $R^2$ is a substituted or unsubstituted furyl. In some embodiments, $R^2$ is an unsubstituted pyridyl. In some embodiments, $R^2$ is an unsubstituted pyridazinyl. In some embodiments, $R^2$ is an unsubstituted pyrimidinyl. In some embodiments, $R^2$ is an unsubstituted thienyl. In some embodiments, $R^2$ is a chloro-substituted thienyl. In some embodiments, $R^2$ is an unsubstituted furyl. In some embodiments, $R^2$ is a substituted or unsubstituted morpholinyl. In some embodiments, $R^2$ is a substituted or unsubstituted oxanyl. In some embodiments, $R^2$ is a substituted or unsubstituted oxetanyl. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or unsubstituted naphthyl. In some embodiments, $R^2$ is unsubstituted benzodioxinyl. In some embodiments, $R^2$ is unsubstituted naphthyl. In some embodiments, $R^2$ is substituted or unsubstituted phenyl. In some embodiments, Y is fluorine.

In some embodiments, the compound has the structure of Formula (IIb). In some embodiments, $L^3$ is a bond, or substituted or unsubstituted alkylene, and $R^3$ is substituted or unsubstituted aryl, substituted or unsubstituted fused ring aryl, substituted or unsubstituted heterocycloalkyl, or substituted or unsubstituted heteroaryl. In some embodiments, $R^3$ is substituted or unsubstituted phenyl, or substituted or unsubstituted thienyl. In some embodiments, $R^3$ is unsubstituted phenyl. In some embodiments, $R^3$ is unsubstituted thienyl. In some embodiments, $R^3$ is a chloro-substituted thienyl. In some embodiments, $R^3$ is substituted or unsubstituted pyridyl, or substituted or unsubstituted pyridazinyl. In some embodiments, $R^3$ is unsubstituted pyridyl. In some embodiments, $R^3$ is unsubstituted pyridazinyl. In some embodiments, $R^3$ is substituted or unsubstituted pyrimidinyl, or substituted or unsubstituted furyl. In some embodiments, $R^3$ is unsubstituted pyrimidinyl. In some embodiments, $R^3$ is unsubstituted furyl. In some embodiments, $R^3$ is substituted or unsubstituted morpholinyl, or substituted or unsubstituted oxanyl, or substituted or unsubstituted oxetanyl. In some embodiments, $R^3$ is unsubstituted morpholinyl. In some embodiments, $R^3$ is unsubstituted oxanyl. In some embodiments, $R^3$ is unsubstituted oxetanyl. In some embodiments, $R^3$ is substituted or unsubstituted benzodioxinyl, or substituted or unsubstituted naphthyl. In some embodiments, $R^3$ is unsubstituted benzodioxinyl. In some embodiments, $R^3$ is unsubstituted naphthyl. In some embodiments, $R^3$ is substituted or unsubstituted phenyl. In some embodiments, Y is fluorine.

In some embodiments, the compound has the structure of Formula (IIb) wherein $L^3$ is —C(O)O—, and $R^3$ is substituted or unsubstituted alkyl, and Y is fluorine.

In some embodiments, the compound has the structure of Formula (IIb) wherein $L^3$ is —C(O)NR$^5$—, $R^5$ is hydrogen or alkyl, and $R^3$ is substituted or unsubstituted alkyl and Y is fluorine.

Further to any embodiment above wherein the compound has the structure of Formula (IIb), in some embodiments, $L^1$ is a bond, —S—, —NR$^4$—, substituted or unsubstituted alkylene, or substituted or unsubstituted heteroalkylene, where $R^4$ is as described in formula Ia and $R^1$ is hydrogen, substituted or unsubstituted alkyl, substituted or unsubstituted aryl, substituted or unsubstituted fused ring aryl, substituted or unsubstituted heteroaryl, or substituted or unsubstituted heterocycloalkyl. In some embodiments, $R^1$ is a substituted or unsubstituted pyridyl. In some embodiments, $R^1$ is a substituted or unsubstituted pyridazinyl. In some embodiments, $R^1$ is a substituted or unsubstituted pyrimidinyl. In some embodiments, $R^1$ is a substituted or unsubstituted thienyl. In some embodiments, $R^1$ is a substituted or unsubstituted furyl. In some embodiments, $R^1$ is an unsubstituted pyridyl. In some embodiments, $R^1$ is an unsubstituted pyridazinyl. In some embodiments, $R^1$ is an unsubstituted pyrimidinyl. In some embodiments, $R^1$ is an unsubstituted thienyl. In some embodiments, $R^1$ is a chloro-substituted thienyl. In some embodiments, $R^1$ is an unsubstituted furyl. In some embodiments, $R^1$ is a substituted or unsubstituted morpholinyl. In some embodiments, $R^1$ is a substituted or unsubstituted oxanyl. In some embodiments, $R^1$ is a substituted or unsubstituted oxetanyl. In some embodiments, $R^1$ is an unsubstituted morpholinyl. In some embodiments, $R^1$ is an unsubstituted oxanyl. In some embodiments, $R^1$ is an unsubstituted oxetanyl. In some embodiments, $R^1$ is substituted or unsubstituted benzodioxinyl. In some embodiments, $R^1$ is substituted or unsubstituted naphthyl. In some embodiments, $R^1$ is unsubstituted benzodioxinyl. In some embodiments, $R^1$ is unsubstituted naphthyl. In some embodiments, $R^1$ is substituted or unsubstituted phenyl. In some embodiments, Y is fluorine.

Further to any embodiment above wherein the compound has the structure of Formula (IIb), in some embodiments, $L^2$ is a bond or substituted or unsubstituted alkylene. In some embodiments, $L^2$ is a bond. In some embodiments, $L^2$ is unsubstituted alkylene. In some embodiments, $L^2$ is substituted alkylene. In some embodiments, $R^2$ is hydrogen. In some embodiments, $R^2$ is substituted or unsubstituted alkyl, or substituted or unsubstituted aryl. Further to any particular $L^2$, in some embodiments $R^2$ is substituted or unsubstituted alkyl, or substituted or unsubstituted aryl. In some embodiments, $R^2$ is unsubstituted alkyl. In some embodiments, $R^2$ is unsubstituted aryl. In some embodiments, $R^3$ is unsubstituted phenyl. In some embodiments, $R^2$ is substituted alkyl. In some embodiments, $R^2$ is substituted aryl. In some embodiments, Y is fluorine.

Further to any embodiment above wherein the compound has the structure of Formula (IIb), in some embodiments, $L^2$ is substituted or unsubstituted alkylene or —C(O)—, and $R^2$ is hydrogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl. In some embodiments, $R^2$ is a substituted or unsubstituted pyridyl. In some embodiments, $R^2$ is a substituted or unsubstituted pyridazinyl. In some embodiments, $R^2$ is a substituted or unsubstituted pyrimidinyl. In some embodiments, $R^2$ is a substituted or unsubstituted thienyl. In some embodiments, $R^2$ is a substituted or unsubstituted furyl. In some embodiments, $R^2$ is an unsubstituted pyridyl. In some embodiments, $R^2$ is an unsubstituted pyridazinyl. In some embodiments, $R^2$ is an unsubstituted pyrimidinyl. In some embodiments, $R^2$ is an unsubstituted thienyl. In some embodiments, $R^2$ is a chloro-substituted thienyl. In some embodiments, $R^2$ is an unsubstituted furyl. In some embodiments, $R^2$ is a substituted or unsubstituted morpholinyl. In some embodiments, $R^2$ is a substituted or unsubstituted oxanyl. In some embodiments, $R^2$ is a substituted or unsubstituted oxetanyl. In some embodiments, $R^2$ is an unsubstituted morpholinyl. In some embodiments, $R^2$ is an unsubstituted oxanyl. In some embodiments, $R^2$ is an unsubstituted oxetanyl. In some embodiments, $R^2$ is substituted or unsubstituted benzodioxinyl. In some embodiments, $R^2$ is substituted or, unsubstituted naphthyl. In some embodiments, $R^2$ is unsubstituted benzodioxinyl. In some embodiments, $R^2$ is unsubstituted naphthyl. In some embodiments, $R^2$ is substituted or unsubstituted phenyl. In some embodiments, Y is fluorine.

Exemplary compounds, e.g., multisubstituted aromatic compounds, in accordance with the present disclosure are provided herein. In Table A following, compound (Cmpd) number, chemical name (i.e., International Union of Pure and Applied Chemistry [IUPAC] name), molecular weight (MW$_{calc}$ calculated mass) and biological activity (i.e., inhibition activity in a thrombin assay) are disclosed.

For Table A following, the disclosed compounds were assayed for inhibition of the protease activity of thrombin as described herein. In Table A, the level of inhibition in the thrombin assay is indicated as follows: a: IC$_{50}$≤0.1 µM; b: 0.1 µM<IC$_{50}$<1 µM; c: IC$_{50}$≥1 µM. Accordingly, in some embodiments, there is provided a compound as expressly set forth in Table A following.

TABLE A

| Cmpd No. | IUPAC Name | MW | Thrombin Activity |
|---|---|---|---|
| 1 | 1-(5-[(5-chlorothiophen-2-yl)methyl]amino-3-(1-[5-(dimethylamino)naphthalen-1-yl]sulfonylpiperidin-4-yl)-4-fluoro-1H-pyrazol-1-yl)-3-hydroxy-2,2-dimethylpropan-1-one | 648 | a |
| 2 | 1-(5-[(5-chlorothiophen-2-yl)methyl]amino-4-fluoro-3-(5-hydroxy-5,6,7,8-tetrahydronaphthalen-2-yl)-1H-pyrazol-1-yl)-2,2-dimethylpropan-1-one | 462 | c |
| 3 | 1-(5-[(5-chlorothiophen-2-yl)methyl]amino-4-fluoro-3-(oxan-4-yl)-1H-pyrazol-1-yl)-2,2-dimethylpropan-1-one | 400 | a |
| 4 | 1-(5-[(5-chlorothiophen-2-yl)methyl]amino-4-fluoro-3-(oxan-4-yl)-1H-pyrazol-1-yl)-3-hydroxy-2,2-dimethylpropan-1-one | 416 | a |
| 5 | 1-(5-[(5-chlorothiophen-2-yl)methyl]amino-4-fluoro-3-(oxan-4-yl)-1H-pyrazol-1-yl)-3-methoxy-2,2-dimethylpropan-1-one | 430 | a |
| 6 | 1-(5-[(5-chlorothiophen-2-yl)methyl]amino-4-fluoro-3-(piperidin-4-yl)-1H-pyrazol-1-yl)-2,2-dimethylpropan-1-one | 399 | a |
| 7 | 1-(5-[(5-chlorothiophen-2-yl)methyl]amino-4-fluoro-3-(piperidin-4-yl)-1H-pyrazol-1-yl)-2-methoxy-2-methylpropan-1-one | 415 | a |
| 8 | 1-(5-[(5-chlorothiophen-2-yl)methyl]amino-4-fluoro-3-(piperidin-4-yl)-1H-pyrazol-1-yl)-3-hydroxy-2,2-dimethylpropan-1-one | 415 | a |
| 9 | 1-(5-[(5-chlorothiophen-2-yl)methyl]amino-4-fluoro-3-(piperidin-4-yl)-1H-pyrazol-1-yl)-3-methoxy-2,2-dimethylpropan-1-one | 429 | a |
| 10 | 1-(5-[(5-chlorothiophen-2-yl)methyl]amino-4-fluoro-3-phenyl-1H-pyrazol-1-yl)-2,2-dimethylpropan-1-one | 392 | a |
| 11 | 1-(5-[(5-chlorothiophen-2-yl)methyl]amino-4-fluoro-3-phenyl-1H-pyrazol-1-yl)-2-hydroxy-2-methylpropan-1-one | 394 | a |
| 12 | 1-(5-[(5-chlorothiophen-2-yl)methyl]amino-4-fluoro-3-phenyl-1H-pyrazol-1-yl)-2-methoxy-2-methylpropan-1-one | 408 | a |
| 13 | 1-(5-[(5-chlorothiophen-2-yl)methyl]amino-4-fluoro-3-phenyl-1H-pyrazol-1-yl)-3-(2-methoxyethoxy)-2,2-dimethylpropan-1-one | 466 | a |
| 14 | 1-(5-[(5-chlorothiophen-2-yl)methyl]amino-4-fluoro-3-phenyl-1H-pyrazol-1-yl)-3-hydroxy-2,2-dimethylpropan-1-one | 408 | a |
| 15 | 1-(5-[(5-chlorothiophen-2-yl)methyl]amino-4-fluoro-3-phenyl-1H-pyrazol-1-yl)-3-methoxy-2,2-dimethylpropan-1-one | 422 | a |
| 16 | 1-[4-(5-[(5-chlorothiophen-2-yl)methyl]amino-1-(2,2-dimethylpropanoyl)-4-fluoro-1H-pyrazol-3-yl)phenyl]pyrrolidin-2-one | 475 | a |
| 17 | 1-[4-(5-[(5-chlorothiophen-2-yl)methyl]amino-1-(2,3-dihydro-1,4-benzodioxine-5-carbonyl)-4-fluoro-1H-pyrazol-3-yl)phenyl]pyrrolidin-2-one | 553 | a |
| 18 | 1-[4-(5-[(5-chlorothiophen-2-yl)methyl]amino-4-fluoro-1-(2-methoxybenzoyl)-1H-pyrazol-3-yl)phenyl]-2,2,2-trifluoroethan-1-ol | 540 | c |
| 19 | 1-[4-(5-[(5-chlorothiophen-2-yl)methyl]amino-4-fluoro-1-(2-methoxybenzoyl)-1H-pyrazol-3-yl)phenyl]pyrrolidin-2-one | 525 | a |
| 20 | 1-[4-(5-[(5-chlorothiophen-2-yl)methyl]amino-4-fluoro-1-(furan-3-carbonyl)-1H-pyrazol-3-yl)phenyl]pyrrolidin-2-one | 485 | c |
| 21 | 1-[4-(5-[(5-chlorothiophen-2-yl)methyl]amino-4-fluoro-1H-pyrazol-3-yl)piperidine-1-carbonyl]cyclopropan-1-ol | 399 | b |
| 22 | 1-[5-(benzylamino)-4-fluoro-3-(pyridin-2-yl)-1H-pyrazol-1-yl]-2,2-dimethylpropan-1-one | 352 | a |
| 23 | 1-[5-(benzylamino)-4-fluoro-3-phenyl-1H-pyrazol-1-yl]-2,2-dimethylpropan-1-one | 351 | a |
| 24 | 1-benzoyl-N-[(5-chlorothiophen-2-yl)methyl]-4-fluoro-3-(oxan-4-yl)-1H-pyrazol-5-amine | 420 | a |
| 25 | 1-benzoyl-N-[(5-chlorothiophen-2-yl)methyl]-4-fluoro-5-(oxan-4-yl)-1H-pyrazol-3-amine | 420 | c |
| 26 | 2-(5-[(5-chlorothiophen-2-yl)methyl]amino-4-fluoro-3-phenyl-1H-pyrazole-1-carbonyl)phenyl 5-(dimethylamino)naphthalene-1-sulfonate | 661 | b |
| 27 | 4-(5-[(5-chlorothiophen-2-yl)methyl]amino-4-fluoro-3-phenyl-1H-pyrazole-1-carbonyl)phenyl 5-(dimethylamino)naphthalene-1-sulfonate | 661 | c |
| 28 | 4-[4-(5-[(5-chlorothiophen-2-yl)methyl]amino-1-(2,2-dimethylpropanoyl)-4-fluoro-1H-pyrazol-3-yl)phenyl]morpholin-3-one | 491 | a |

TABLE A-continued

| Cmpd No. | IUPAC Name | MW | Thrombin Activity |
|---|---|---|---|
| 29 | 6-(5-[(5-chlorothiophen-2-yl)methyl]amino-1-(2,2-dimethylpropanoyl)-4-fluoro-1H-pyrazol-3-yl)-1,2,3,4-tetrahydronaphthalen-1-one | 460 | a |
| 30 | 6-(5-[(5-chlorothiophen-2-yl)methyl]amino-4-fluoro-1-(2-methoxybenzoyl)-1H-pyrazol-3-yl)-1,2,3,4-tetrahydronaphthalen-1-ol | 512 | c |
| 31 | 6-(5-[(5-chlorothiophen-2-yl)methyl]amino-4-fluoro-1-(2-methoxybenzoyl)-1H-pyrazol-3-yl)-1,2,3,4-tetrahydronaphthalen-1-one | 510 | a |
| 32 | N-[(5-chlorothiophen-2-yl)methyl]-1-(2,3-dihydro-1,4-benzodioxine-5-carbonyl)-4-fluoro-3-(oxan-4-yl)-1H-pyrazol-5-amine | 478 | a |
| 33 | N-[(5-chlorothiophen-2-yl)methyl]-1-(2,3-dihydro-1,4-benzodioxine-5-carbonyl)-4-fluoro-3-(piperidin-4-yl)-1H-pyrazol-5-amine | 477 | a |
| 34 | N-[(5-chlorothiophen-2-yl)methyl]-1-(2,3-dihydro-1,4-benzodioxine-5-carbonyl)-4-fluoro-3-phenyl-1H-pyrazol-5-amine | 470 | a |
| 35 | N-[(5-chlorothiophen-2-yl)methyl]-1-(2,3-dihydro-1,4-benzodioxine-5-carbonyl)-4-fluoro-5-(oxan-4-yl)-1H-pyrazol-3-amine | 478 | c |
| 36 | N-[(5-chlorothiophen-2-yl)methyl]-1-(2,4-dimethoxybenzoyl)-4-fluoro-3-(oxan-4-yl)-1H-pyrazol-5-amine | 480 | a |
| 37 | N-[(5-chlorothiophen-2-yl)methyl]-1-(2,4-dimethoxybenzoyl)-4-fluoro-3-(piperidin-4-yl)-1H-pyrazol-5-amine | 479 | a |
| 38 | N-[(5-chlorothiophen-2-yl)methyl]-1-(2,4-dimethoxybenzoyl)-4-fluoro-3-phenyl-1H-pyrazol-5-amine | 472 | a |
| 39 | N-[(5-chlorothiophen-2-yl)methyl]-1-(2,4-dimethoxybenzoyl)-4-fluoro-5-(oxan-4-yl)-1H-pyrazol-3-amine | 480 | c |
| 40 | N-[(5-chlorothiophen-2-yl)methyl]-3-(1-[5-(dimethylamino)naphthalen-1-yl]sulfonylpiperidin-4-yl)-4-fluoro-1-(2-methoxybenzoyl)-1H-pyrazol-5-amine | 682 | c |
| 41 | N-[(5-chlorothiophen-2-yl)methyl]-4-fluoro-1-(2-methoxybenzoyl)-3-(oxan-4-yl)-1H-pyrazol-5-amine | 450 | a |
| 42 | N-[(5-chlorothiophen-2-yl)methyl]-4-fluoro-1-(2-methoxybenzoyl)-3-(piperidin-4-yl)-1H-pyrazol-5-amine | 449 | a |
| 43 | N-[(5-chlorothiophen-2-yl)methyl]-4-fluoro-1-(2-methoxybenzoyl)-3-(pyridin-2-yl)-1H-pyrazol-5-amine | 443 | a |
| 44 | N-[(5-chlorothiophen-2-yl)methyl]-4-fluoro-1-(2-methoxybenzoyl)-3-phenyl-1H-pyrazol-5-amine | 442 | a |
| 45 | N-[(5-chlorothiophen-2-yl)methyl]-4-fluoro-1-(2-methoxybenzoyl)-5-(oxan-4-yl)-1H-pyrazol-3-amine | 450 | c |
| 46 | N-[(5-chlorothiophen-2-yl)methyl]-4-fluoro-1-(3-methyloxetane-3-carbonyl)-3-phenyl-1H-pyrazol-5-amine | 406 | c |
| 47 | N-[(5-chlorothiophen-2-yl)methyl]-4-fluoro-1-(4-methyloxane-4-carbonyl)-3-(oxan-4-yl)-1H-pyrazol-5-amine | 442 | a |
| 48 | N-[(5-chlorothiophen-2-yl)methyl]-4-fluoro-1-(4-methyloxane-4-carbonyl)-3-phenyl-1H-pyrazol-5-amine | 434 | a |
| 49 | N-[(5-chlorothiophen-2-yl)methyl]-4-fluoro-1-(furan-3-carbonyl)-3-(oxan-4-yl)-1H-pyrazol-5-amine | 410 | a |
| 50 | N-[(5-chlorothiophen-2-yl)methyl]-4-fluoro-1-(furan-3-carbonyl)-3-(piperidin-4-yl)-1H-pyrazol-5-amine | 409 | a |
| 51 | N-[(5-chlorothiophen-2-yl)methyl]-4-fluoro-1-(furan-3-carbonyl)-3-phenyl-1H-pyrazol-5-amine | 402 | a |
| 52 | N-[(5-chlorothiophen-2-yl)methyl]-4-fluoro-1-[4-(2-methoxyethoxy)benzoyl]-3-(oxan-4-yl)-1H-pyrazol-5-amine | 494 | a |
| 53 | N-[(5-chlorothiophen-2-yl)methyl]-4-fluoro-1-[4-(morpholin-4-yl)benzoyl]-3-(oxan-4-yl)-1H-pyrazol-5-amine | 505 | a |
| 54 | N-[(5-chlorothiophen-2-yl)methyl]-4-fluoro-3-(oxan-4-yl)-1-(thiophene-3-carbonyl)-1H-pyrazol-5-amine | 426 | a |
| 55 | N-[(5-chlorothiophen-2-yl)methyl]-5-(1-[5-(dimethylamino)naphthalen-1-yl]sulfonylpiperidin-4-yl)-4-fluoro-1-(2-methoxybenzoyl)-1H-pyrazol-3-amine | 682 | c |
| 56 | N-[(5-chlorothiophen-2-yl)methyl]-N-[4-fluoro-3-(5-oxo-5,6,7,8-tetrahydronaphthalen-2-yl)-1H-pyrazol-5-yl]-2-methoxybenzamide | 510 | c |
| 57 | N-[4-(5-[(5-chlorothiophen-2-yl)methyl]amino-4-fluoro-3-(piperidin-4-yl)-1H-pyrazole-1-carbonyl)phenyl]-5-(dimethylamino)naphthalene-1-sulfonamide | 667 | a |
| 58 | N-[4-(5-[(5-chlorothiophen-2-yl)methyl]amino-4-fluoro-3-phenyl-1H-pyrazole-1-carbonyl)phenyl]-5-(dimethylamino)naphthalene-1-sulfonamide | 660 | a |
| 59 | N-benzyl-4-fluoro-1-(2-methoxybenzoyl)-3-(pyridin-2-yl)-1H-pyrazol-5-amine | 402 | a |

TABLE A-continued

| Cmpd No. | IUPAC Name | MW | Thrombin Activity |
|---|---|---|---|
| 60 | N-benzyl-4-fluoro-1-(2-methoxybenzoyl)-3-phenyl-1H-pyrazol-5-amine | 401 | a |
| 61 | [1-(5-[(5-chlorothiophen-2-yl)methyl]amino-4-fluoro-3-(oxan-4-yl)-1H-pyrazole-1-carbonyl)cyclopropyl]methanol | 414 | a |
| 62 | [1-(5-[(5-chlorothiophen-2-yl)methyl]amino-4-fluoro-3-phenyl-1H-pyrazole-1-carbonyl)cyclopropyl]methanol | 406 | a |

Compounds disclosed herein also include racemic mixtures, stereoisomers and mixtures of the compounds, including isotopically-labeled and radio-labeled compounds. See e.g., Goding, 1986, MONOCLONAL ANTIBODIES PRINCIPLES AND PRACTICE; Academic Press, p. 104. Such isomers can be isolated by standard resolution techniques, including e.g., fractional crystallization, chiral chromatography, and the like. See e.g., Eliel, E. L. & Wilen S. H., 1993, STEREOCHEMISTRY IN ORGANIC COMPOUNDS; John Wiley & Sons, New York.

In some embodiments, compounds disclosed herein have asymmetric centers and can occur as racemates, racemic mixtures, and as individual enantiomers or diastereoisomers, with all isomeric forms as well as mixtures thereof being contemplated for use in the compounds and methods described herein. The compounds contemplated for use in the compounds and methods described herein do not include those that are known in the art to be too unstable to synthesize and/or isolate.

The compounds disclosed herein can also contain unnatural proportions of atomic isotopes at one or more of the atoms that constitute such compounds. For example, the compounds can be radiolabeled with radioactive isotopes, such as for example tritium ($^{3}H$), iodine-125 ($^{125}I$), or carbon-14 ($^{14}C$). All isotopic variations of the compounds disclosed herein, whether radioactive or not, are encompassed within the contemplated scope.

In some embodiments, metabolites of the compounds disclosed herein are useful for the methods disclosed herein.

In some embodiments, compounds contemplated herein are provided in the form of a prodrug. The term "prodrug" refers to a compound that can be converted into a compound (e.g., a biologically active compound) described herein in vivo. Prodrugs can be useful for a variety of reason known in the art, including e.g., ease of administration due e.g., to enhanced bioavailable in oral administration, and the like. The prodrug can also have improved solubility in pharmaceutical compositions over the biologically active compounds. An example, without limitation, of a prodrug is a compound which is administered as an ester (i.e., the "prodrug") to facilitate transmittal across a cell membrane where water solubility is detrimental to mobility but which then is metabolically hydrolyzed to the carboxylic acid, the active entity, once inside the cell where water-solubility is beneficial. Conventional procedures for the selection and preparation of suitable prodrug derivatives are described, for example, in DESIGN OF PRODRUGS, (ed. H. Bundgaard, Elsevier, 1985), which is hereby incorporated herein by reference for the limited purpose describing procedures and preparation of suitable prodrug derivatives.

Accordingly, in some embodiments, compounds contemplated herein are provided in the form of a prodrug ester. The term "prodrug ester" refers to derivatives of the compounds disclosed herein formed by the addition of any of a variety of ester-forming groups, e.g., groups known in the art, that are hydrolyzed under physiological conditions. Examples of prodrug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "Pro-drugs as Novel Delivery Systems", Vol. 14, A.C.S. Symposium Series, American Chemical Society (1975); and BIOREVERSIBLE CARRIERS IN DRUG DESIGN: THEORY AND APPLICATION, edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

In some embodiments, prodrugs can be slowly converted to the compounds described herein useful for the methods described herein when placed in a transdermal patch reservoir with a suitable enzyme or chemical reagent.

Certain compounds disclosed herein can exist in unsolvated forms as well as solvated forms, including hydrated forms. In general, the solvated forms are equivalent to unsolvated forms and are encompassed within the scope of contemplated compounds. Certain compounds of the present invention can exist in multiple crystalline or amorphous forms. In general, all physical forms are equivalent for the compounds and methods contemplated herein and are intended to be within the scope disclosed herein.

III. Biological Activities

In some embodiments, compounds described herein exhibit inhibitory activity against thrombin with activities 1 µM, e.g., about 1, 2, 3, 4, 5, 6, 7, 8, 9, 10, 11, 12, 13, 14, 16, 18, 20, 22, 24, 26, 28, 30, 32, 34, 36, 38, 40, 45, 50, 55, 60, 65, 70, 75, 80, 85, 90, 95, 100 µM, or even greater. In some embodiments, the compounds exhibit inhibitory activity against thrombin with activities between 0.1 µM and 1 µM, e.g., about 0.1, 0.2, 0.3, 0.4, 0.5, 0.6, 0.7, 0.8, 0.9 or 1.0 µM. In some embodiments, compounds described herein exhibit inhibitory activity against thrombin with activities 0.1 µM, e.g., about 1, 2, 5, 10, 15, 20, 30, 40, 50, 60, 70, 80, 90, or 100 nM. Ranges of values using a combination of any of the values recited herein as upper and/or lower limits are also contemplated, for example, but not limited to, 1-10 nM, 10-100 nM, 0.1-1 µM, 1-100 µM, 100-200 µM, 200-500 µM or even 500-1000 µM. In some embodiments, the inhibitory activity is in the range of about 1-10 nM, 10-100 nM, 0.1-1 µM, 1-10 µM, 10-100 µM, 100-200 µM, 200-500 µM, or even 500-1000 µM. It is understood that for purposes of quantification, the terms "activity," "inhibitory activity," "biological activity," "thrombin activity" and the like in the context of an inhibitory compound disclosed herein can be quantified in a variety of ways known in the art. Unless indicated otherwise, as used herein such terms refer to $IC_{50}$ in the customary sense (i.e., concentration to achieve half-maximal inhibition).

Inhibitory activity against thrombin in turn inhibits the blood coagulation process. Accordingly, compounds disclosed herein are indicated in the treatment or management of thrombotic disorders. In some embodiments, a dose or a therapeutically effective dose of a compound disclosed herein will be that which is sufficient to achieve a plasma concentration of the compound or its active metabolite(s) within a range set forth herein, e.g., about 1-10 nM, 10-100 nM, 0.1-1 µM, 1-10 µM, 10-100 µM, 100-200 µM, 200-500 µM, or even 500-1000 µM, preferably about 1-10 nM, 10-100 nM, or 0.1-1 µM. Without wishing to be bound by any theory, it is believe that such compounds are indicated in the treatment or management of thrombotic disorders.

IV. Methods of Treating and Preventing Disease

Thrombosis.

Thrombotic diseases are the primary indications for thrombin inhibition, because of thrombin's location in the coagulation cascade and, in turn, the importance of the coagulation cascade in the progression of blood clotting processes. However, without wishing to be bound by any theory, it is believed the coagulation cascade in general, and thrombin in particular, is important in a variety other disease states.

It has been discovered that compounds described herein, e.g., multisubstituted aromatic compounds, exhibit inhibitory action against thrombin (activated blood-coagulation factor II; EC 3.4.21.5). This, in turn inhibits the blood coagulation process.

This inhibitory action is useful in the treatment of a variety of thrombotic disorders, such as, but not limited to, acute vascular diseases such as acute coronary syndromes; venous-, arterial- and cardiogenic thromboembolisms; the prevention of other states such as disseminated intravascular coagulation, or other conditions that involve the presence or the potential formation of a blood clot thrombus. Other indications for methods described herein include the following.

Cancer.

It has long been recognized that cancer progression is accompanied by venous thrombosis, but it has not been understood how each disease is related. From several clinical trials studying the treatment of VTE, metaanalyses have shown that low molecular weight heparins (LMWHs) improve overall survival in subgroups of cancer patients. See e.g., Zacharski, L. R. & Lee, A. Y., 2008, *Expert Opin Investig Drugs*, 17:1029-1037; Falanga, A. & Piccioli, A., 2005, *Current Opinion in Pulmonary Medicine*, 11:403-407; Smorenburg, S. M., et al., 1999, *Thromb Haemost*, 82:1600-1604; Hettiarachchi, R. J., et al., 1999, *Thromb Haemost*, 82:947-952. This finding was substantiated in later clinical trials that measured specifically the survival of cancer patients. See e.g., Lee, A. Y. et al., 2005, *J Clin Oncol*, 23:2123-2129; Klerk, C. P. et al., *J Clin Oncol* 2005, 23:2130-2135; Kakkar, A. K., et al., 2004, *J Clin Oncol*, 22:1944-1948; Altinbas, M., et al., 2004, *J Thromb Haemost*, 2:1266-1271.

More recently, researchers have focused on the specific anticancer effect of DTIs. For example, it was shown that heparin significantly prolonged the survival of patients with limited small cell lung cancer. See e.g., Akl, E. A., et al., 2008, *J Exp Clin Cancer Res*, 27:4. Other investigators found that systemic use of argatroban reduced tumor mass and prolonged survival time in rat glioma models leading to the conclusion that argatroban should be considered as a novel therapeutic for glioma, a notoriously difficult to treat cancer type. See e.g., Hua, Y., et al., 2005, *Acta Neurochir, Suppl* 2005, 95:403-406; Hua, Y., et al., 2005, *J Thromb Haemost*, 3:1917-1923. Very recently, it was demonstrated that dabigatran etexilate, a DTI recently FDA-approved (see e.g., Hughes, B., 2010, *Nat Rev Drug Discov*, 9:903-906) for DVT indications, inhibited both the invasion and metastasis of malignant breast tumors. See e.g., DeFeo, K. et al., 2010, *Thrombosis Research*, 125 (Supplement 2): S188-S188; Defeo, K., et al., 2010, *Cancer Biol Ther*, 10:1001-1008. Thus, dabigatran etexilate treatment led to a 50% reduction in tumor volume at 4 weeks with no weight loss in treated mice. Dabigatran etexilate also reduced tumor cells in the blood and liver micrometastases by 50-60%. These investigators concluded that dabigatran etexilate can be beneficial in not only preventing thrombotic events in cancer patients, but also as adjunct therapy to treat malignant tumors.

Further, hirudin and the LMWH nadroparin dramatically reduced the number of lung metastases when administered prior to cancer cell inoculation. See e.g., Hu, L., et al., 2004, *Blood*, 104:2746-51.

The de novo thrombin inhibitor d-Arg-Oic-Pro-d-Ala-Phe (p-Me) has been found to block thrombin-stimulated invasion of prostate cancer cell line PC-3 in a concentration dependent manner. See e.g., Nieman, M. T., et al., 2008, *J Thromb Haemost*, 6:837-845. A reduced rate of tumor growth was observed in mice dosed with the pentapeptide through their drinking water. The mice also showed reduced fold rate in tumor size and reduced overall tumor weight compared to untreated mice. Microscopic examination of treated tumors showed reduced number of large blood vessels thus concluding that the pentapeptide interfered with tumor angiogenesis. Nieman, M. T., et al., *Thromb Haemost*, 104:1044-8.

In view of these and related studies, it is suggested that anticoagulants affect tumor metastasis; that is, angiogenesis, cancer cell adhesion, migration and invasion processes. See e.g., Van Noorden, C. J., et al., 2010, *Thromb Res*, 125 Suppl 2:S77-79.

Fibrosis.

Several studies have shown the utility of anticoagulant therapy in fibrotic disorders. For example, in a rat model of $CCl_4$-induced chronic liver injury, the DTI SSR182289 decreased liver fibrogenesis significantly after 7 weeks of administration. Similar observations were made in other studies using the LMWHs nadroparin, tinzaparin, enoxaparin, and dalteparin sodium. See e.g., Duplantier, J. G., et al., 2004, *Gut*, 53:1682-1687; Abdel-Salam, O. M., et al., 2005, *Pharmacol Res*, 51:59-67; Assy, N., et al., 2007, *Dig Dis Sci*, 52:1187-1193; Abe, W., et al., 2007, *J Hepatol*, 46:286-294.

In another example, the DTI melagatran greatly reduced ischemia reperfusion injury in a kidney transplant model in the large white pig. This led to a drastically improved kidney graft survival at 3 months. See e.g., Favreau, F., et al., 2010, *Am J Transplant*, 10:30-39.

Recent studies have shown that in a bleomycin-induced mouse model of pulmonary fibrosis, dabigatran etexilate treatment reduced important profibrotic events in lung fibroblasts, including the production of collagen and connective tissue growth factor. See e.g., Silver, R. M., et al., 2010, *Am. J. Respir. Crit. Care Med.*, 181:A6780; Bogatkevich, G. S., et al., 2009, *Arthritis Rheum*, 60:3455-3464.

The above experimental evidence points to a close relationship between thrombin and fibrosis and suggests novel therapeutic opportunities for fibrosis using thrombin inhibitors. See e.g., Calvaruso, V., et al., 2008, *Gut*, 57:1722-1727; Chambers, R. C., 2008, *Br J Pharmacol*, 153 Suppl 1:S367-

378; Chambers, R. C. & Laurent, G. J., 2002, *Biochem Soc Trans*, 30:194-200; Howell, D. C., et al., 2001, *Am J Pathol*, 159:1383-1395.

Alzheimer's Disease.

Very recent experiments confirm higher thrombin levels in brain endothelial cells of patients with Alzheimer's disease. While 'normal' thrombin levels are connected to regulatory CNS functions, thrombin accumulation in the brain is toxic. It has also been found that the neural thrombin inhibitor Protease Nexin 1 (PN-1) is significantly reduced in the Alzheimer's disease brain, despite the fact that PN-1 mRNA levels are unchanged. These observations have led some investigators to suggest that reduction of CNS-resident thrombin will prove useful in Alzheimer's Disease (AD) treatment. See e.g., Vaughan, P. J., et al., 1994, *Brain Res*, 668:160-170; Yin, X., et al., 2010, *Am J Pathol*, 176:1600-1606; Akiyama, H., et al., 1992, *Neurosci Lett*, 146:152-154.

Multiple Sclerosis.

Investigators found that hirudin treatment in an animal model of Multiple Sclerosis (MS) showed a dramatic improvement in disease severity. See e.g., Han, M. H., et al., 2008, *Nature*, 451:1076-1081. Similar results were obtained following treatment with heparin (a DTI) and dermatan sulfate another coagulation inhibitor. See e.g., Chelmicka-Szorc, E. & Amason, B. G., 1972, *Arch Neurol*, 27:153-158; Inaba, Y., et al., 1999, *Cell Immunol*, 198:96-102. Other evidence shows that naturally occurring antithrombin III has anti-inflammatory effects in diseases such as endotoxemia and other sepsis-related conditions. See e.g., Wiedermann, C. J. & Romisch, J., 2002, *Acta Med Austriaca*, 29:89-92. Naturally occurring thrombin inhibitors are presumably synthesized in situ and have protective roles in CNS inflammation. Therefore, therapeutic thrombin inhibition has been proposed as a potential MS treatment. See e.g., Luo, W., et al., 2009, In: THROMBIN, Maragoudakis, M. E.; Tsopanoglou, N. E., Eds. Springer New York: 2009; pp 133-159.

Pain.

In a rat pain model with partial lesion of the sciatic nerve, intrathecal hirudin prevented the development of neuropathic pain and curbed pain responses for 7 days. The investigators found that following injury, neuropathic pain was mediated by thrombin generation, which in turn activated PAR-1 receptor in the spinal cord. Hirudin inhibited thrombin generation and ultimately led to pain relief. See e.g., Garcia, P. S., et al., 2010, *Thromb Haemost*, 103:1145-1151; Narita, M., et al., 2005, *J Neurosci*, 25:10000-10009. Researchers hypothesize that thrombin and the PARs are involved not just as part of the coagulation cascade, but in inflammation, nociception and neurodevelopment. Development of a DTI to intersect an unexploited pharmacology will lead to pain therapeutics distinct from opioids and NSAIDs, whose shortcomings are well documented. See e.g., Garcia 2010, *Id*.

Accordingly, in a further aspect, there is provided a method for treating a disease or disorder in a subject in need thereof. The method includes administering a compound of any of Formulae (Ia), (Ib), (IIa) or (IIb) as disclosed herein, a compound as set forth in Table A, pharmaceutically acceptable salt, ester, solvate, or prodrug thereof, or pharmaceutical composition thereof, to a subject in need thereof in an amount effective to treat the disease or disorder. The terms "therapeutically effective amount," "amount effective to treat," "amount effective to prevent" and the like refer to that amount of drug or pharmaceutical agent (e.g., compound or pharmaceutical composition disclosed herein) that will elicit the biological or medical response of a tissue, system, animal, or human that is being sought by a researcher, veterinarian, medical doctor or other clinician.

In some embodiments, the disease or disorder is a thrombotic disease or disorder. In some embodiments, the thrombotic disease or disorder is acute coronary syndrome, venous thromboembolism, arterial thromboembolism or cardiogenic thromboembolism. In some embodiments, the thrombotic disease or disorder is acute coronary syndrome. In some embodiments, the thrombotic disease or disorder is venous thromboembolism. In some embodiments, the thrombotic disease or disorder is arterial thromboembolism. In some embodiments, the thrombotic disease or disorder is cardiogenic thromboembolism.

In some embodiments, the disease or disorder is fibrosis, Alzheimer's Disease, multiple sclerosis, pain, or cancer. In some embodiments, the disease or disorder is Alzheimer's Disease. In some embodiments, the disease or disorder is multiple sclerosis.

In some embodiments, the disease or disorder is fibrosis. In some embodiments contemplating fibrosis, the method is directed to treating chronic liver injury. In some embodiments, the disease or disorder is ischemia reperfusion injury. In some embodiments, the disease or disorder is pulmonary fibrosis.

In some embodiments, the disease or disorder is pain. In some embodiments, the pain is neuropathic pain.

In some embodiments, the disease or disorder is cancer. In some embodiments, the cancer is limited small cell lung cancer. In some embodiments, the cancer is a glioma. In some embodiments, the cancer is malignant breast cancer. In some embodiments, the cancer is a micrometastasis. In some embodiments, the micrometastasis is of the blood or liver. In some embodiments, the cancer is a lung metastasis. In some embodiments, the cancer is prostatic cancer.

In another aspect, there is provided a method for preventing a disease or disorder in a subject. The method includes administering a compound of any of Formulae (Ia), (Ib), (IIa) or (IIb) as disclosed herein, compound as set forth in Table A herein, pharmaceutically acceptable salt, ester, solvate, or prodrug thereof, or pharmaceutical composition thereof, to a subject in need thereof in an amount effective to prevent the disease or disorder.

In some embodiments, the disease or disorder is a thrombotic disorder. In some embodiments, the thrombotic disorder is acute coronary syndrome, venous thromboembolism, arterial thromboembolism or cardiogenic thromboembolism. In some embodiments, the thrombotic disease or disorder is disseminated intravascular coagulation. In some embodiments, the thrombotic disorder involves the presence or the potential formation of a blood clot thrombus.

Yet further to this aspect, in some embodiments, the disease or disorder is fibrosis, Alzheimer's Disease, multiple sclerosis, pain, or cancer. In some embodiments, the disease or disorder is fibrosis. In some embodiments, the disease or disorder is Alzheimer's Disease. In some embodiments, the disease or disorder is multiple sclerosis. In some embodiments, the disease or disorder is pain. In some embodiments, the disease or disorder is cancer.

V. Assays

Compounds described herein can be assayed, by a variety of methods known in the art and described herein, for inhibition of biological activity, e.g., protease activity, of a variety of proteins, e.g., thrombin. For example, the protease activity of such proteins, e.g., thrombin, can be monitored using a chromophoric substrate, e.g., a p-nitroanilide peptide substrate, which upon hydrolysis releases p-nitroanilide, which in turn gives rise to a color change which can be determined spectrophotometrically. See e.g., Lottenberg, R, et al., 1983, *Biochemica et Biophysica Acta,* 752:539-557. Accordingly, the change in color can be monitored with a spectrophotometer at e.g., 405 nm to provide a signal which is directly proportional to the proteolytic activity of the enzyme.

The thrombin activity reported herein (e.g., Table A) was obtained as follows. Human thrombin was obtained from Haematologic Technologies Inc. The chromogenic substrate S-2238 was obtained from DiaPharma. Thrombin was assayed in buffer containing 0.05 M Tris (pH 7.4), 0.015 M NaCl and 0.01% PEG-8000. The final concentration of enzyme used was 3 nM thrombin. The final concentration of substrate used was 125 µM S-2238 for thrombin. All assays were performed in 96-well microtiter plates at room temperature (RT). The enzyme and inhibitor were pre-incubated for 10 minutes then substrate was added and read at 405 nm in a SpectraMax Plus Spectrophotometer (Molecular Devices). Inhibitor $IC_{50}$ values were determined by adding test compound as ten point, three-fold serial dilutions in buffer solution, as known in the art. The plate was read at 10 minutes after substrate addition. The $IC_{50}$ was calculated by plotting the percent (%) inhibition against compound concentration and fitting the data to a constrained four parameter sigmoidal curve, as known in the art.

VI. Pharmaceutical Compositions

In another aspect, there is provided a pharmaceutical composition comprising a compound disclosed herein and a pharmaceutically acceptable excipient. The compound is a compound of any of Formulae (Ia), (Ib), (IIa) or (IIb) as disclosed herein, a compound as set forth in Table A herein, or pharmaceutically acceptable salt, ester, solvate, or prodrug thereof. In some embodiments, the compound is set forth in Table A herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds disclosed herein contain both basic and acidic functionalities that allow the compounds to be converted into either base or acid addition salts.

Compounds disclosed herein can exist as salts, such as with pharmaceutically acceptable acids. Accordingly, the compounds contemplated herein include such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts can be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Pharmaceutically acceptable salts of the compounds above, where a basic or acidic group is present in the structure, are also included within the scope of compounds contemplated herein. When an acidic substituent is present, such as —NHSO$_3$H, —COOH and —P(O)(OH)$_2$, there can be formed the ammonium, sodium, potassium, calcium salt, and the like, for use as the dosage form. Basic groups, such as amino or basic heteroaryl radicals, or pyridyl and acidic salts, such as hydrochloride, hydrobromide, acetate, maleate, palmoate, methanesulfonate, p-toluenesulfonate, and the like, can be used as the dosage form.

Also, in the embodiments in which R—COOH is present, pharmaceutically acceptable esters can be employed, e.g., methyl, ethyl, tert-butyl, pivaloyloxymethyl, and the like, and those esters known in the art for modifying solubility or hydrolysis characteristics for use as sustained release or prodrug formulations.

A. Formulations

The compounds disclosed herein can be prepared and administered in a wide variety of oral, parenteral, and topical dosage forms. Thus, the compounds can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds disclosed herein can be administered transdermally. It is also envisioned that multiple routes of administration (e.g., intramuscular, oral, transdermal) can be used to administer the compounds disclosed herein. In some embodiments, the compounds disclosed herein can be administered orally as tablets, aqueous or oily suspensions, lozenges, troches, powders, granules, emulsions, capsules, syrups or elixirs. The composition for oral use can contain one or more agents selected from the group of sweetening agents, flavoring agents, coloring agents and preserving agents in order to produce pharmaceutically elegant and palatable preparations. Accordingly, there are also provided pharmaceutical compositions comprising a pharmaceutically acceptable carrier or excipient and one or more compounds disclosed herein.

In some embodiments, tablets contain the acting ingredient in admixture with non-toxic pharmaceutically acceptable excipients that are suitable for the manufacture of tablets. These excipients can be, for example, (1) inert diluents, such as calcium carbonate, lactose, calcium phosphate, carboxymethylcellulose, or sodium phosphate; (2) granulating and disintegrating agents, such as corn starch or alginic acid;

(3) binding agents, such as starch, gelatin or acacia; and (4) lubricating agents, such as magnesium stearate, stearic acid or talc. These tablets can be uncoated or coated by known techniques to delay disintegration and absorption in the gastrointestinal tract and thereby provide a sustained action over a longer period. For example, a time delay material such as glyceryl monostearate or glyceryl distearate can be employed.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substance that can also act as diluents, flavoring agents, binders, preservatives, tablet disintegrating agents, or an encapsulating material.

A compound disclosed herein, in the form of a free compound or a pharmaceutically-acceptable pro-drug, metabolite, analogue, derivative, solvate or salt, can be administered, for in vivo application, parenterally by injection or by gradual perfusion over time. Administration can be intravenously, intraperitoneally, intramuscularly, subcutaneously, intracavity, or transdermally. For in vitro studies the compounds can be added or dissolved in an appropriate biologically acceptable buffer and added to a cell or tissue.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds disclosed herein are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds disclosed herein can also be incorporated into liposomes or administered via transdermal pumps or patches. Pharmaceutical admixtures suitable for use in the pharmaceuticals compositions and methods disclosed herein include those described, for example, in PHARMACEUTICAL SCIENCES (17th Ed., Mack Pub. Co., Easton, Pa.) and WO 96/05309, the teachings of both of which are hereby incorporated by reference.

In some embodiments, preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, growth factors and inert gases and the like.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations can contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation can be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds can have limited solubility in water and therefore can require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions can be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions disclosed herein can additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

By the present, there are provided methods for ameliorating wound healing and for mediating tissue repair (including but not limited to treatment of peripheral and coronary vascular disease). According to these methods, a subject having a wound or in need of tissue repair, is treated at the site of the wound or damaged tissue or treated systemically, with a compound disclosed herein in the form of a free compound or a pharmaceutically-acceptable prodrug, metabolite, analogue, derivative, solvate or salt.

Generally, the terms "treating", "treatment" and the like are used herein to mean affecting a subject, tissue or cell to obtain a desired pharmacologic and/or physiologic effect. The effect can be prophylactic in terms of completely or partially preventing a disease or disorder or sign or symptom thereof, and/or can be therapeutic in terms of a partial or complete cure for a disorder and/or adverse effect attributable to it. "Treating" as used herein covers any treatment of, or prevention of a disease or disorder in a vertebrate, a mammal, particularly a human, and includes: (a) preventing the disease or disorder from occurring in a subject that can be predisposed to the disease or disorder, but has not yet been diagnosed as having it; (b) inhibiting the disease or disorder, i.e., arresting its development; or (c) relieving or ameliorating the disease or disorder, i.e., cause regression of the disease or disorder.

There are provided various pharmaceutical compositions useful for ameliorating diseases and disorders, including thrombosis. In some embodiments, the disease or disorder is a thrombotic disorder. In some embodiments, the disease or disorder is acute coronary syndrome, venous thromboembolism, arterial thromboembolism or cardiogenic thromboembolism. In some embodiments, the disease or disorder is fibrosis. In some embodiments, the disease or disorder is Alzheimer's Disease. In some embodiments, the disease or disorder is multiple sclerosis. In some embodiments, the disease or disorder is pain. In some embodiments, the disease or disorder is cancer. The pharmaceutical compositions according to one embodiment are prepared by formulating a compound disclosed herein in the form of a free compound or a pharmaceutically-acceptable pro-drug, metabolite, analogue, derivative, solvate or salt, either alone or together with other pharmaceutical agents, suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See e.g., Goodman and Gilman (eds.), 1990, THE PHARMACOLOGICAL BASIS FOR THERAPEUTICS (7th ed.).

The pharmaceutical compositions are preferably prepared and administered in dose units. Solid dose units are tablets, capsules and suppositories. For treatment of a subject, depending on activity of the compound, manner of administration, nature and severity of the disease or disorder, age and body weight of the subject, different daily doses can be used.

Under certain circumstances, however, higher or lower daily doses can be appropriate. The administration of the daily dose can be carried out both by single administration in the form of an individual dose unit or else several smaller dose units and also by multiple administrations of subdivided doses at specific intervals.

The pharmaceutical compositions contemplated herein can be administered locally or systemically in a therapeutically effective dose. Amounts effective for this use will, of course, depend on the severity of the disease or disorder and the weight and general state of the subject. Typically, dosages used in vitro can provide useful guidance in the amounts useful for in situ administration of the pharmaceutical composition, and animal models can be used to determine effective dosages for treatment of particular disorders.

Various considerations are described, e.g., in Langer, 1990, *Science,* 249: 1527; Goodman and Gilman's (eds.), 1990, Id., each of which is herein incorporated by reference and for all purposes. Dosages for parenteral administration of active pharmaceutical agents can be converted into corresponding dosages for oral administration by multiplying parenteral dosages by appropriate conversion factors. As to general applications, the parenteral dosage in mg/m2 times 1.8=the corresponding oral dosage in milligrams ("mg"). As to oncology applications, the parenteral dosage in mg/m2 times 1.6=the corresponding oral dosage in mg. An average adult weighs about 70 kg. See e.g., Miller-Keane, 1992, ENCYCLOPEDIA & DICTIONARY OF MEDICINE, NURSING & ALLIED HEALTH, 5th Ed., (W. B. Saunders Co.), pp. 1708 and 1651.

The method by which the compound disclosed herein can be administered for oral use would be, for example, in a hard gelatin capsule wherein the active ingredient is mixed with an inert solid diluent, or soft gelatin capsule, wherein the active ingredient is mixed with a co-solvent mixture, such as PEG 400 containing Tween-20. A compound disclosed herein can also be administered in the form of a sterile injectable aqueous or oleaginous solution or suspension. The compound can generally be administered intravenously or as an oral dose of 0.1 ug to 20 mg/kg given, for example, every 3-12 hours.

Formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients can be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which can be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions can be in the form of a sterile injectable aqueous or oleagenous suspension. This suspension can be formulated according to known methods using those suitable dispersing or wetting agents and suspending agents that have been mentioned above. The sterile injectable preparation can also a sterile injectable solution or suspension in a non-toxic parenterally-acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

A compound disclosed herein can also be administered in the form of suppositories for rectal administration of the drug. These compositions can be prepared by mixing the drug with a suitable non-irritating excipient that is solid at ordinary temperature but liquid at the rectal temperature and will therefore melt in the rectum to release the drug. Such materials include cocoa butter and polyethylene glycols.

The compounds disclosed herein as used in the methods disclosed herein can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds disclosed herein, are employed.

In addition, some of the compounds disclosed herein can form solvates with water or common organic solvents. Such solvates are encompassed within the scope of the methods contemplated herein.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat thrombosis, such compositions will contain an amount of active ingredient effective to achieve the desired result (e.g. decreasing the extent of the thrombosis).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to inhibition of thrombin); presence of other diseases or other health-related problems; kind of concurrent treatment; and complications from any disease or treatment regimen. Other therapeutic regimens or agents can be used in conjunction with the methods and compounds disclosed herein.

For any compound described herein, the therapeutically effective amount can be initially determined from a variety of techniques known in the art, e.g., biochemical characterization of inhibition of thrombin, cell culture assays, and the like. Target concentrations will be those concentrations of active compound(s) that are capable of decreasing thrombin enzymatic activity as measured, for example, using the methods described.

Therapeutically effective amounts for use in humans can be determined from animal models. For example, a dose for humans can be formulated to achieve a concentration that has been found to be effective in animals. The dosage in humans can be adjusted by monitoring thrombin inhibition and adjusting the dosage upwards or downwards, as described above.

Dosages can be varied depending upon the requirements of the patient and the compound being employed. The dose administered to a patient, in the context of the methods disclosed herein, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments of a method disclosed herein, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

Accordingly, in some embodiments, dosage levels of the compounds disclosed herein as used in the present methods are of the order of e.g., about 0.1 mg to about 1 mg, about 1 mg to about 10 mg, about 0.5 mg to about 20 mg per kilogram body weight, an average adult weighing 70 kilograms, with a preferred dosage range between about 0.1 mg to about 20 mg per kilogram body weight per day (from about 0.7 mg to about 1.4 gm per patient per day). The amount of the compound disclosed herein that can be combined with the carrier materials to produce a single dosage will vary depending upon the host treated and the particular mode of administration. For example, a formulation intended for oral administration to humans can contain about 5 ug to 1 g of a compound disclosed herein with an appropriate and convenient amount of carrier material that can vary from about 5 to 95 percent of the total composition. Dosage unit forms will generally contain between from about 0.1 mg to 500 mg of a compound disclosed herein.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from in vitro assays, cell culture assays and/or animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual practitioner in view of the patient's condition and the particular method in which the compound is used. For in vitro formulations, the exact formulation and dosage can be chosen by the individual practitioner in view of the patient's condition and the particular method in which the compound is used.

VII. Examples

The examples below are meant to illustrate certain embodiments of the invention and not to limit the scope of the invention. Abbreviations used herein have their conventional meaning in the art, unless indicated otherwise. Specific abbreviations include the following: Å=Ångström; $Ac_2O$=acetic anhydride; AcOH=acetic acid; aq=aqueous; Bt=benzotriazole; BOC=N-tert-butoxycarbonyl; br=broad; t-BuOH=tert-butanol; ° C.=degree Celsius; d=doublet; DABCO=1,4-diazabicyclo[2.2.2]octane; DCE=1,2-dichloroethane; DCM=dichloromethane; dd=doublet of doublets; DIEA=diethylisopropylamine; DMAP=4-dimethylaminopyridine; DMF=N,N-dimethylformamide; DMSO=dimethylsulfoxide; δ=chemical shift (given in ppm, unless otherwise indicated); EDCI=1-ethyl-3-(3-dimethylaminopropyl)carbodiimide; eq=equivalent; $Et_2O$=diethyl ether; $Et_3N$=triethylamine; EtOAc=ethyl acetate; EtOH=ethanol; g=gram; h (or hr)=hour; HOBt=hydroxybenzotriazole; HPLC=high performance liquid chromatography; Hz=Hertz; $IC_{50}$=inhibitory concentration at 50% inhibition; J=coupling constant (given in Hz, unless otherwise indicated); LC=liquid chromatography; LHMDS=lithium hexamethyldisilazide; m=multiplet; M=molar; $[M+H]^+$=parent mass spectrum peak plus $H^+$; MS=mass spectrum; ms=molecular sieves; MP=melting point; $Me_2NH$=dimethylamine; MeOH=methanol; mg=milligram; mL=milliliter; mM=millimolar; mmol=millimole; min=minute; μL=microliter; μM=micromolar; ng=nanogram; nM=nanomolar; NMR=nuclear magnetic resonance; ppm=parts per million; q=quartet; $R_f$=retention factor; RT=room temperature; s=singlet; t=triplet; TFA=trifluoroacetic acid; THF=tetrahydrofuran; TLC=thin layer chromatography.

Example 1—Preparation of Intermediate 1

General Scheme I.

A synthetic scheme useful for synthesis of compounds described herein is disclosed in General Scheme I following, wherein the terms "$R^x$", "$R^y$", and "$R^z$" are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted heterocycloalkenyl, substituted or unsubstituted aryl, or substituted or unsubstituted heteroaryl, or other groups obvious to those skilled in the art.

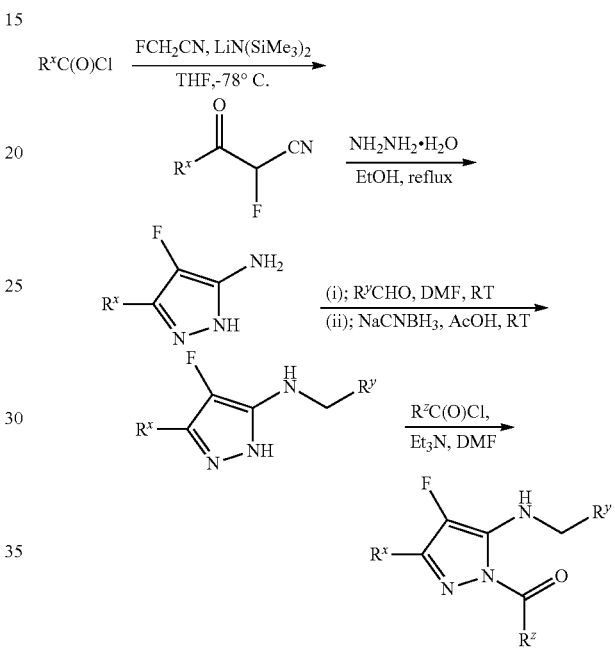

The synthesis of Intermediate 1 followed General Procedure 1 following.

General Procedure 1

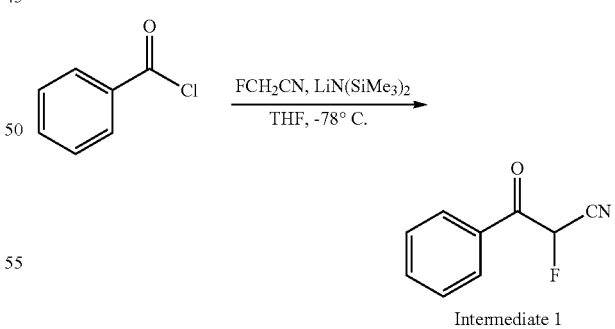

Intermediate 1

To a cold (−78° C.) solution of benzoyl chloride (5.0 mmol, 1.0 eq) and fluoroacetonitrile (278 μL, 5.0 mmol, 1.0 eq) in dry THF (15 mL) was added a solution of LHMDS in THF (1 M, 10 mL, 10.0 mmol, 2.0 eq). The mixture was allowed to reach room temperature, and 1N HCl was added dropwise achieving pH 2. The mixture was concentrated under reduced pressure to afford intermediate 1 in a form pure enough for the next step.

Example 2—Preparation of Intermediate 2

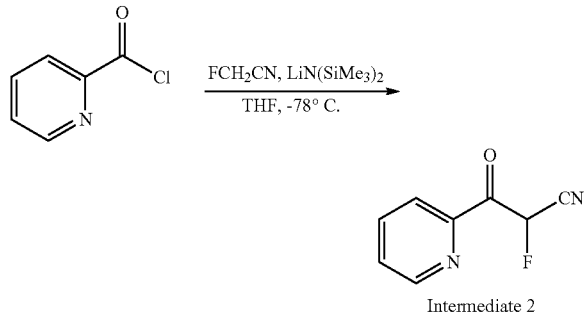

Intermediate 2

General Procedure 1 was followed to obtain Intermediate 2. Thus, to a cold (−78° C.) solution of picolinoyl chloride (5.0 mmol, 1.0 eq) and fluoroacetonitrile (278 μL, 5.0 mmol, 1.0 eq) in dry THF (15 mL) was added a solution of LHMDS in THF (1 M, 10 mL, 10.0 mmol, 2.0 eq). The mixture was allowed to reach room temperature, and 1N HCl was added dropwise achieving pH 2. The mixture was concentrated under reduced pressure to afford intermediate 2 in a form pure enough for the next step.

Example 3—Preparation of Intermediate 3

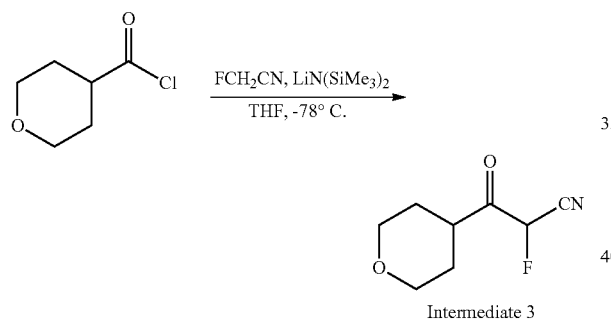

Intermediate 3

General Procedure 1 was followed to obtain Intermediate 3. Thus, to a cold (−78° C.) solution of pyran-4-carbonyl chloride (5.0 mmol, 1.0 eq) and fluoroacetonitrile (278 μL, 5.0 mmol, 1.0 eq) in dry THF (15 mL) was added a solution of LHMDS in THF (1 M, 10 mL, 10.0 mmol, 2.0 eq). The mixture was allowed to reach room temperature, and 1N HCl was added dropwise achieving pH 2. The mixture was concentrated under reduced pressure to afford intermediate 3 in a form pure enough for the next step.

Example 4—Preparation of Intermediate 4

The synthesis of Intermediate 4 followed the procedure of General Procedure 2 following.
General Procedure 2

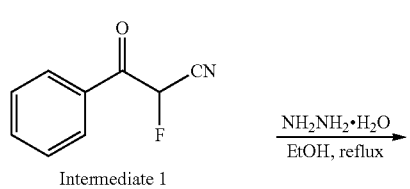

Intermediate 1

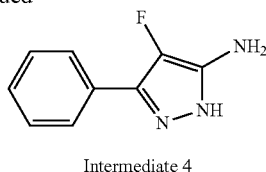

Intermediate 4

To a solution of intermediate 1 (5.0 mmol) in ethanol (15 mL) was added hydrazine monohydrate (582 μL, 12.0 mmol, 2.4 eq). The reaction was heated at reflux for 18 h. The reaction mixture was allowed to cool to room temperature, and the solvent was evaporated under reduced pressure. The residue was dissolved in dichloromethane (DCM) and washed with water. The organic phase was concentrated to give a crude product that was purified by silica column, yielding intermediate 4 as a light brown solid (0.56 g, 55%). NMR (400 MHz, DMSO-$d_6$) δ (ppm): 4.80 (s, 2H), 7.28-7.32 (m, 1H), 7.41-7.45 (m, 2H), 7.62-7.64 (m, 2H), 11.88 (s, 1H).

Example 5—Preparation of Intermediate 5

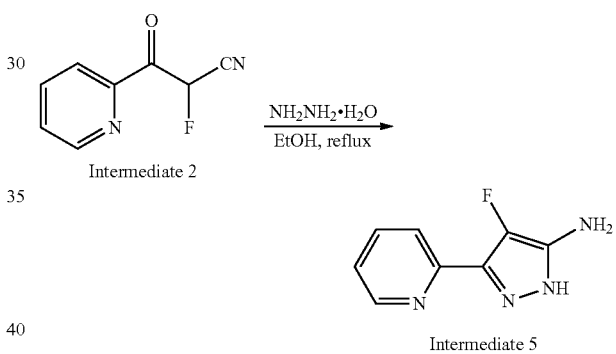

Intermediate 5

General Procedure 2 was followed to convert Intermediate 2 to Intermediate 5

Example 6—Preparation of Intermediate 6

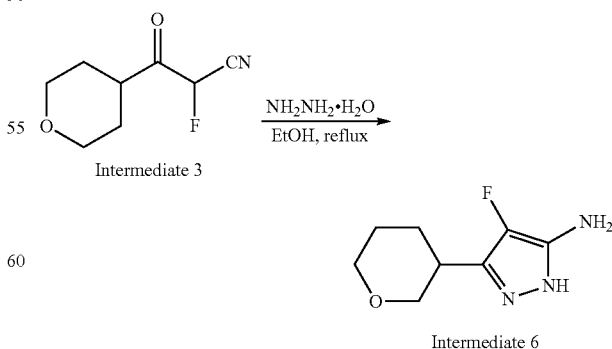

Intermediate 6

General Procedure 2 was followed to convert Intermediate 3 to Intermediate 6

Example 7—Preparation of Intermediate 7

The synthesis of Intermediate 7 followed the procedure of General Procedure 3 following.

General Procedure 3

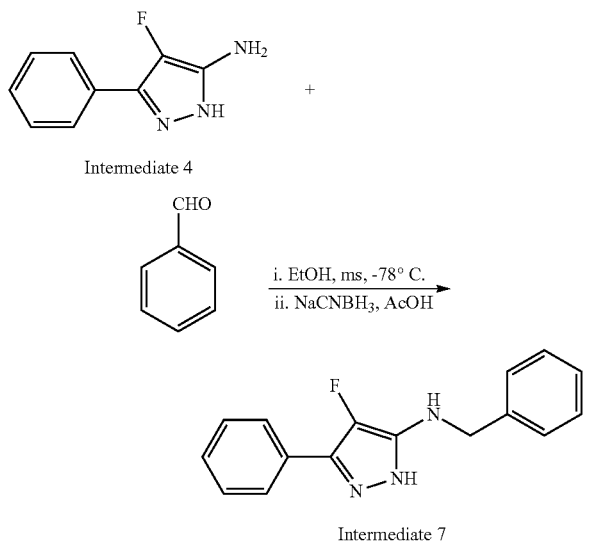

Intermediate 7

A solution of intermediate 4 (12.4 mmol) and benzaldehyde (24.8 mmol, 2 eq) in EtOH (20 mL) with molecular sieves (4 Å powder) was refluxed for 8 h. Then was added a catalytic quantity of AcOH, NaCNBH$_3$ (1.6 g, 24.8 mmol, 2 eq) at 0° C. with stirring for 15 h at RT. The solvent was distilled off, and the residue was dissolved in EtOAc (200 mL) and filtered through a Celite® pad to remove inorganic materials. The filtrate was washed with saturated aqueous NaHCO$_3$ (2×20 mL), water (20 mL), brine (20 mL), dried over Na$_2$SO$_4$, filtered and concentrated in vacuo. The resultant compound was purified by column chromatography over silica gel (100-200 mesh) by using a solvent gradient of 0-10% MeOH—CHCl$_3$ as the eluent to afford Intermediate 7.

Example 8—Preparation of Intermediate 8

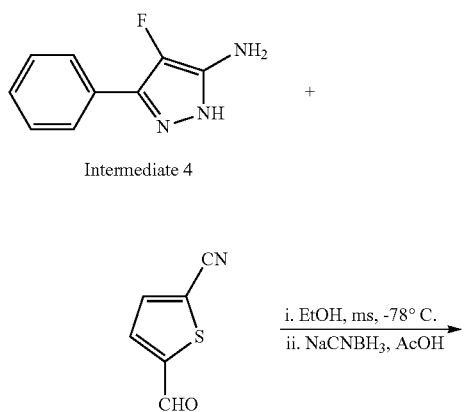

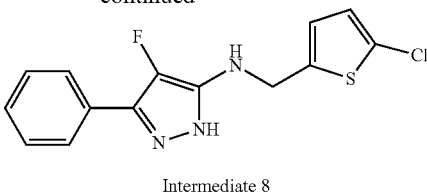

Intermediate 8

General Procedure 3 was followed to convert Intermediate 4 to Intermediate 8

Example 9—Preparation of Compound 23

The synthesis of Compound 23 followed the procedure of General Procedure 4 following.

General Procedure 4

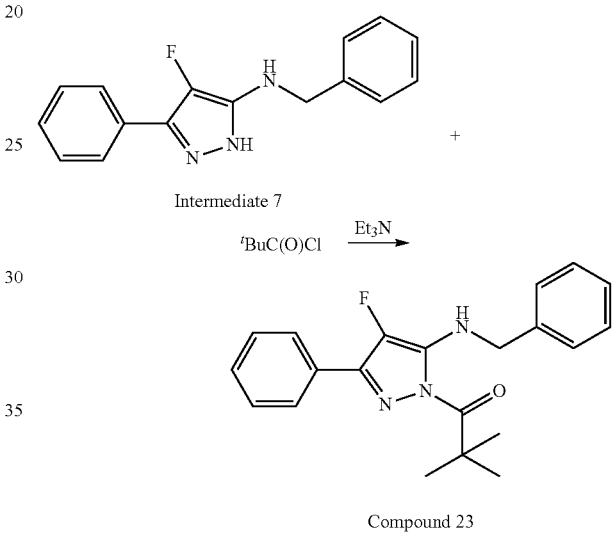

Compound 23

Pivaloyl chloride was added to a solution of Intermediate 7 in triethylamine (3 mL) at RT and stirred for 5 h. The reaction mixture was diluted with water (5 mL) and extracted with EtOAc (20 mL). The organic layer washed with water (2×5 mL), saturated aqueous NaHCO$_3$ (5 brine (5 mL), dried over Na$_2$SO$_4$, filtered and concentrated in vacuo. The crude compound was purified by column chromatography over silica gel (100-200 mesh) by using a gradient mixture of 0-30% EtOAc-hexane as the eluent to afford Compound 23 (33%). MP 105-106° C.; H NMR: (DMSO-d$_6$) δ 7.77 (d, J=7.4 Hz, 2H), 7.56-7.60 (m, 1H), 7.41-7.52 (m, 3H), 7.33-7.38 (m, 4H), 7.25 (br s, 1H), 4.53 (d, J=6.2 Hz, 2H), 1.48 (s, 9N); MS: 352 [M+H]$^+$.

Example 10—Preparation of Compound 10

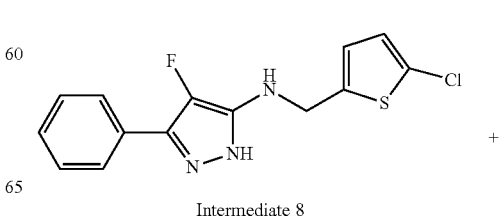

Intermediate 8

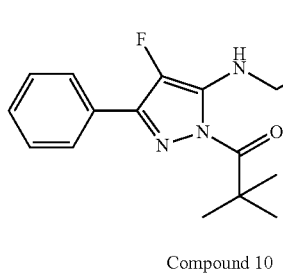

Compound 10

General Procedure 4 was followed to convert Intermediate 8 to Compound 10. Thus, pivaloyl chloride was added to a solution of Intermediate 8 in triethylamine (3 mL) at RT and stirred for 5 h. The reaction mixture was diluted with water (5 mL) and extracted with EtOAc (20 mL). The organic layer washed with water (2×5 mL), saturated aqueous NaHCO$_3$ (5 mL), brine (5 mL), dried over Na$_2$SO$_4$, filtered and concentrated in vacuo. The crude compound was purified by column chromatography over silica gel (100-200 mesh) by using a gradient mixture of 0-30% EtOAc-hexane as the eluent to afford Compound 10 (35%). NMR: (CDCl$_3$) δ 7.8-7.9 (m, 2H), 7.40-7.48 (m, 3H), 7.10-7.18 (m, 1H), 6.74-6.81 (m, 2H), 4.63 (d, J=6.2 Hz, 2H), 1.53 (s, 9H); MS: 392 [M+H]$^+$.

Example 11—Preparation of Intermediate 9

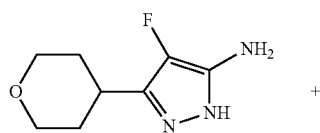

Intermediate 6

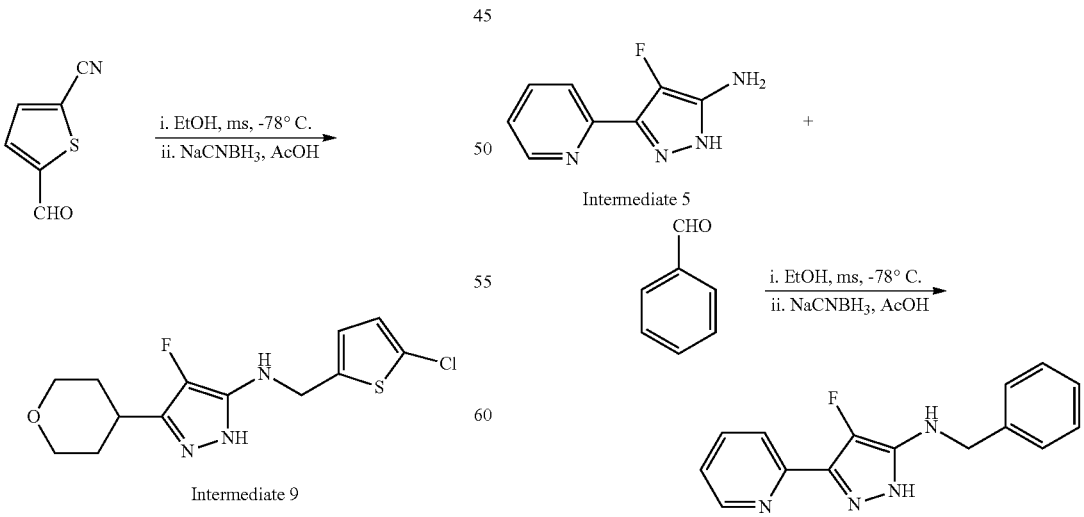

General Procedure 3 was followed to convert Intermediate 6 to Intermediate 9

Example 12—Preparation of Compound 3

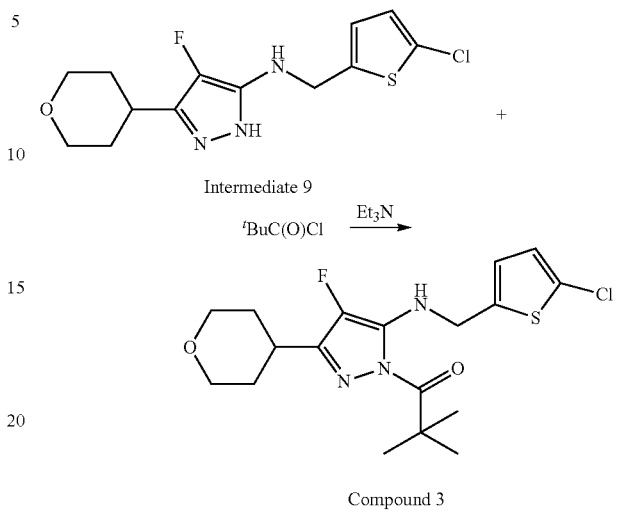

Compound 3

General Procedure 4 was followed to convert Intermediate 9 to Compound 3. Thus, pivaloyl chloride was added to a solution of Intermediate 9 in triethylamine (3 mL) at RT and stirred for 5 h. The reaction mixture was diluted with water (5 mL) and extracted with EtOAc (20 mL). The organic layer washed with water (2×5 mL), saturated aqueous NaHCO$_3$ (5 mL), brine (5 mL), dried over Na$_2$SO$_4$, filtered and concentrated in vacuo. The crude compound was purified by column chromatography over silica gel (100-200 mesh) by using a gradient mixture of 0-30% EtOAc-hexane as the eluent to afford Compound 3 (46%). $^1$H NMR: (CDCl$_3$) δ 7.03 (t, J=7.0 Hz, 1H), 6.75 (br s, 2H), 4.54 (d, J=6.2 Hz, 2H), 4.01-4.06 (m, 2H), 3.50-3.57 (m, 2H), 2.89-2.93 (m, 1H), 1.87-1.91 (m, 4H), 1.44 (s, 9H); MS: 400 [M+H]$^+$.

Example 13—Preparation of Intermediate 10

General Procedure 3 was followed to convert Intermediate 5 to Intermediate 10

Example 14—Preparation of Compound 22

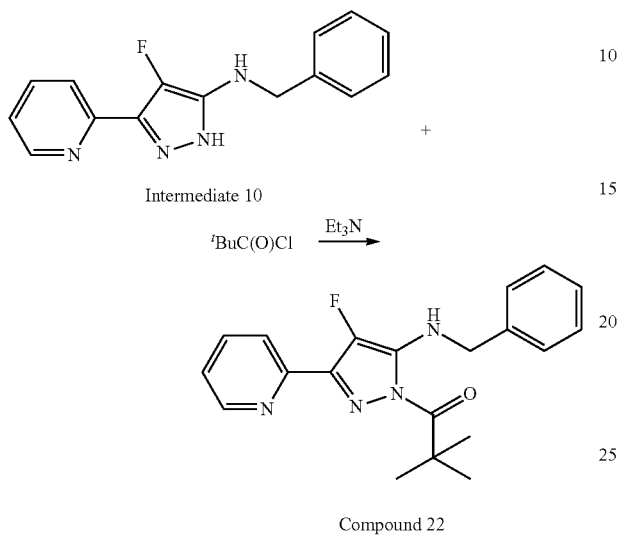

General Procedure 4 was followed to convert Intermediate 10 to Compound 22. Thus, pivaloyl chloride was added to a solution of Intermediate 10 in triethylamine (3 mL) at RT and stirred for 5 h. The reaction mixture was diluted with water (5 mL) and extracted with EtOAc (20 mL). The organic layer washed with water (2×5 mL), saturated aqueous NaHCO$_3$ (5 mL), brine (5 mL), dried over Na$_2$SO$_4$, filtered and concentrated in vacuo. The crude compound was purified by column chromatography over silica gel (100-200 mesh) by using a gradient mixture of 0-30% EtOAc-hexane as the eluent to afford Compound 22 (40%). $^1$H NMR: (DMSO-d$_6$) δ 8.6 (m, 1H), 7.83-7.91 (m, 2H), 7.55 (m, 1H), 7.25-7.45 (m, 6H), 4.52-4.54 (m, 2H), 1.48 (s, 9H); MS: 353.03 [M+H]$^+$.

The contents of all references, patents, and published applications cited herein are hereby incorporated by reference in their entirety and for all purposes.

While the invention has been described in detail with reference to certain preferred embodiments thereof, it will be understood that modifications and variations are within the spirit and scope of that which is described and claimed.

What is claimed is:

1. A compound with structure of Formula (IIa) or (IIb):

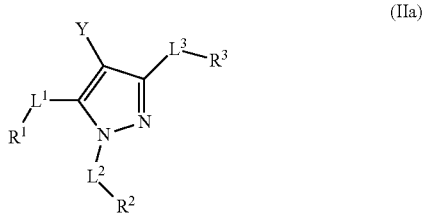

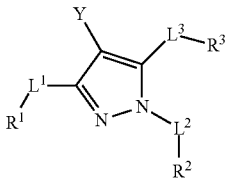

or pharmaceutically acceptable salt, ester, solvate, or prodrug thereof;
wherein
L$^1$ is —NR$^4$—;
L$^2$ is —C(═O)—;
L$^3$ is a bond, substituted or unsubstituted alkylene, substituted or unsubstituted heteroalkylene, —S—, —SO—, —SO$_2$—, —O—, —NHSO$_2$—, or —NR$^4$—;
R$^1$ is substituted alkyl having one or more substituent groups, wherein any substituent group for said R$^1$ substituted alkyl is selected from the group consisting of —OH, —NH$_2$, —SH, —CN, —CF$_3$, —NO$_2$, halogen, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
R$^2$ is hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
R$^3$ is hydrogen, halogen, substituted or unsubstituted alkyl, substituted or unsubstituted heteroalkyl, substituted or unsubstituted cycloalkyl, substituted or unsubstituted cycloalkenyl, substituted or unsubstituted heterocycloalkyl, substituted or unsubstituted heterocycloalkenyl, substituted or unsubstituted aryl, substituted or unsubstituted fused ring aryl, or substituted or unsubstituted heteroaryl;
R$^4$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted cycloalkenyl, substituted or unsubstituted heterocycloalkenyl, and substituted or unsubstituted fused ring aryl or substituted or unsubstituted heteroaryl; and
Y is halogen.

2. The compound according to claim 1, with structure of Formula (IIa), wherein L$^3$ is a bond, substituted or unsubstituted alkylene, or substituted or unsubstituted heteroalkylene, and R$^3$ is substituted or unsubstituted alkyl, substituted or unsubstituted aryl, substituted or unsubstituted fused ring aryl, substituted or unsubstituted heterocycloalkyl, or substituted or unsubstituted heteroaryl.

3. The compound according to claim 1, with structure of Formula (IIa), wherein Y is fluorine.

4. The compound according to claim 2, wherein Y is fluorine.

5. The compound according to claim 2, wherein R$^3$ is substituted or unsubstituted phenyl or substituted or unsubstituted heteroaryl.

6. The compound according to claim 5, wherein $R^3$ is substituted or unsubstituted heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

7. The compound according to claim 6, wherein $R^3$ is chloro-substituted thienyl.

8. The compound according to claim 2, wherein $R^3$ is substituted or unsubstituted heterocycloalkyl selected from the group consisting of substituted or unsubstituted morpholinyl, substituted or unsubstituted oxanyl, and substituted or unsubstituted oxetanyl.

9. The compound according to claim 2, wherein $R^3$ is substituted or unsubstituted fused ring aryl selected from the group consisting of substituted or unsubstituted benzodioxinyl and substituted or unsubstituted naphthyl.

10. The compound according to claim 2, wherein $R^1$ is substituted alkyl having at least one substituted or unsubstituted heteroaryl substituent selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

11. The compound according to claim 10, wherein $R^1$ is substituted alkyl having at least one chloro-substituted thienyl substituent.

12. The compound according to claim 2, wherein $R^1$ is substituted alkyl having at least one substituted or unsubstituted heterocycloalkyl substituent selected from the group consisting of substituted or unsubstituted morpholinyl, substituted or unsubstituted oxanyl, and substituted or unsubstituted oxetanyl.

13. The compound according to claim 2, wherein $R^1$ is substituted alkyl having at least one substituted or unsubstituted fused ring aryl substituent selected from the group consisting of substituted or unsubstituted benzodioxinyl and substituted or unsubstituted naphthyl.

14. The compound according to claim 2, wherein $R^1$ is substituted alkyl having at least one substituted or unsubstituted phenyl substituent.

15. The compound according to claim 2, wherein $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted fused ring aryl, or substituted or unsubstituted heteroaryl.

16. The compound according to claim 15, wherein $R^2$ is substituted or unsubstituted heteroaryl selected from the group consisting of substituted or unsubstituted pyridyl, substituted or unsubstituted pyridazinyl, substituted or unsubstituted pyrimidinyl, substituted or unsubstituted thienyl, and substituted or unsubstituted furyl.

17. The compound according to claim 15, wherein $R^2$ is substituted or unsubstituted alkyl, substituted or unsubstituted cycloalkyl, or substituted or unsubstituted heterocycloalkyl.

18. The compound according to claim 17, wherein $R^2$ is substituted or unsubstituted heterocycloalkyl selected from the group consisting of substituted or unsubstituted morpholinyl, substituted or unsubstituted oxanyl, and substituted or unsubstituted oxetanyl.

19. The compound according to claim 15, wherein $R^2$ is substituted or unsubstituted fused ring aryl selected from the group consisting of substituted or unsubstituted benzodioxinyl and substituted or unsubstituted naphthyl.

20. The compound according to claim 15, wherein $R^2$ is substituted or unsubstituted phenyl.

21. The compound according to claim 1 selected from:
1-(5-{[(5-chlorothiophen-2-yl)methyl]amino}-3-(1-{[5-(dimethylamino)naphthalen-1-yl]sulfonyl}piperidin-4-yl)-4-fluoro-1H-pyrazol-1-yl)-3-hydroxy-2,2-dimethylpropan-1-one;
1-(5-{[(5-chlorothiophen-2-yl)methyl]amino}-4-fluoro-3-(5-hydroxy-5,6,7,8-tetrahydronaphthalen-2-yl)-1H-pyrazol-1-yl)-2,2-dimethylpropan-1-one;
1-(5-{[(5-chlorothiophen-2-yl)methyl]amino}-4-fluoro-3-(oxan-4-yl)-1H-pyrazol-1-yl)-2,2-dimethylpropan-1-one;
1-(5-{[(5-chlorothiophen-2-yl)methyl]amino}-4-fluoro-3-(oxan-4-yl)-1H-pyrazol-1-yl)-3-hydroxy-2,2-dimethylpropan-1-one;
1-(5-{[(5-chlorothiophen-2-yl)methyl]amino}-4-fluoro-3-(oxan-4-yl)-1H-pyrazol-1-yl)-3-methoxy-2,2-dimethylpropan-1-one;
1-(5-{[(5-chlorothiophen-2-yl)methyl]amino}-4-fluoro-3-(piperidin-4-yl)-1H-pyrazol-1-yl)-2,2-dimethylpropan-1-one;
1-(5-{[(5-chlorothiophen-2-yl)methyl]amino}-4-fluoro-3-(piperidin-4-yl)-1H-pyrazol-1-yl)-2-methoxy-2-methylpropan-1-one;
1-(5-{[(5-chlorothiophen-2-yl)methyl]amino}-4-fluoro-3-(piperidin-4-yl)-1H-pyrazol-1-yl)-3-hydroxy-2,2-dimethylpropan-1-one;
1-(5-{[(5-chlorothiophen-2-yl)methyl]amino}-4-fluoro-3-(piperidin-4-yl)-1H-pyrazol-1-yl)-3-methoxy-2,2-dimethylpropan-1-one;
1-(5-{[(5-chlorothiophen-2-yl)methyl]amino}-4-fluoro-3-phenyl-1H-pyrazol-1-yl)-2,2-dimethylpropan-1-one;
1-(5-{[(5-chlorothiophen-2-yl)methyl]amino}-4-fluoro-3-phenyl-1H-pyrazol-1-yl)-2-hydroxy-2-methylpropan-1-one;
1-(5-{[(5-chlorothiophen-2-yl)methyl]amino}-4-fluoro-3-phenyl-1H-pyrazol-1-yl)-2-methoxy-2-methylpropan-1-one;
1-(5-{[(5-chlorothiophen-2-yl)methyl]amino}-4-fluoro-3-phenyl-1H-pyrazol-1-yl)-3-(2-methoxyethoxy)-2,2-dimethylpropan-1-one;
1-(5-{[(5-chlorothiophen-2-yl)methyl]amino}-4-fluoro-3-phenyl-1H-pyrazol-1-yl)-3-hydroxy-2,2-dimethylpropan-1-one;
1-(5-{[(5-chlorothiophen-2-yl)methyl]amino}-4-fluoro-3-phenyl-1H-pyrazol-1-yl)-3-methoxy-2,2-dimethylpropan-1-one;
1-[4-(5-{[(5-chlorothiophen-2-yl)methyl]amino}-1-(2,2-dimethylpropanoyl)-4-fluoro-1H-pyrazol-3-yl)phenyl]pyrrolidin-2-one;
1-[4-(5-{[(5-chlorothiophen-2-yl)methyl]amino}-1-(2,3-dihydro-1,4-benzodioxine-5-carbonyl)-4-fluoro-1H-pyrazol-3-yl)phenyl]pyrrolidin-2-one;
1-[4-(5-{[(5-chlorothiophen-2-yl)methyl]amino}-4-fluoro-1-(2-methoxybenzoyl)-1H-pyrazol-3-yl)phenyl]-2,2,2-trifluoroethan-1-ol;
1-[4-(5-{[(5-chlorothiophen-2-yl)methyl]amino}-4-fluoro-1-(2-methoxybenzoyl)-1H-pyrazol-3-yl)phenyl]pyrrolidin-2-one;
1-[4-(5-{[(5-chlorothiophen-2-yl)methyl]amino}-4-fluoro-1-(furan-3-carbonyl)-1H-pyrazol-3-yl)phenyl]pyrrolidin-2-one;
1-[5-(benzylamino)-4-fluoro-3-(pyridin-2-yl)-1H-pyrazol-1-yl]-2,2-dimethylpropan-1-one;
1-[5-(benzylamino)-4-fluoro-3-phenyl-1H-pyrazol-1-yl]-2,2-dimethylpropan-1-one;

1-benzoyl-N-[(5-chlorothiophen-2-yl)methyl]-4-fluoro-3-(oxan-4-yl)-1H-pyrazol-5-amine;
1-benzoyl-N-[(5-chlorothiophen-2-yl)methyl]-4-fluoro-5-(oxan-4-yl)-1H-pyrazol-3-amine;
2-(5-{[(5-chlorothiophen-2-yl)methyl]amino}-4-fluoro-3-phenyl-1H-pyrazole-1-carbonyl)phenyl 5-(dimethylamino)naphthalene-1-sulfonate;
4-(5-{[(5-chlorothiophen-2-yl)methyl]amino}-4-fluoro-3-phenyl-1H-pyrazole-1-carbonyl)phenyl 5-(dimethylamino)naphthalene-1-sulfonate;
4-[4-(5-{[(5-chlorothiophen-2-yl)methyl]amino}-1-(2,2-dimethylpropanoyl)-4-fluoro-1H-pyrazol-3-yl)phenyl]morpholin-3-one;
6-(5-{[(5-chlorothiophen-2-yl)methyl]amino}-1-(2,2-dimethylpropanoyl)-4-fluoro-1H-pyrazol-3-yl)-1,2,3,4-tetrahydronaphthalen-1-one;
6-(5-{[(5-chlorothiophen-2-yl)methyl]amino}-4-fluoro-1-(2-methoxybenzoyl)-1H-pyrazol-3-yl)-1,2,3,4-tetrahydronaphthalen-1-ol;
6-(5-{[(5-chlorothiophen-2-yl)methyl]amino}-4-fluoro-1-(2-methoxybenzoyl)-1H-pyrazol-3-yl)-1,2,3,4-tetrahydronaphthalen-1-one;
N-[(5-chlorothiophen-2-yl)methyl]-1-(2,3-dihydro-1,4-benzodioxine-5-carbonyl)-4-fluoro-3-(oxan-4-yl)-1H-pyrazol-5-amine;
N-[(5-chlorothiophen-2-yl)methyl]-1-(2,3-dihydro-1,4-benzodioxine-5-carbonyl)-4-fluoro-3-(piperidin-4-yl)-1H-pyrazol-5-amine;
N-[(5-chlorothiophen-2-yl)methyl]-1-(2,3-dihydro-1,4-benzodioxine-5-carbonyl)-4-fluoro-3-phenyl-1H-pyrazol-5-amine;
N-[(5-chlorothiophen-2-yl)methyl]-1-(2,3-dihydro-1,4-benzodioxine-5-carbonyl)-4-fluoro-5-(oxan-4-yl)-1H-pyrazol-3-amine;
N-[(5-chlorothiophen-2-yl)methyl]-1-(2,4-dimethoxybenzoyl)-4-fluoro-3-(oxan-4-yl)-1H-pyrazol-5-amine;
N-[(5-chlorothiophen-2-yl)methyl]-1-(2,4-dimethoxybenzoyl)-4-fluoro-3-(piperidin-4-yl)-1H-pyrazol-5-amine;
N-[(5-chlorothiophen-2-yl)methyl]-1-(2,4-dimethoxybenzoyl)-4-fluoro-3-phenyl-1H-pyrazol-5-amine;
N-[(5-chlorothiophen-2-yl)methyl]-1-(2,4-dimethoxybenzoyl)-4-fluoro-5-(oxan-4-yl)-1H-pyrazol-3-amine;
N-[(5-chlorothiophen-2-yl)methyl]-3-(1-{[5-(dimethylamino)naphthalen-1-yl]sulfonyl}piperidin-4-yl)-4-fluoro-1-(2-methoxybenzoyl)-1H-pyrazol-5-amine;
N-[(5-chlorothiophen-2-yl)methyl]-4-fluoro-1-(2-methoxybenzoyl)-3-(oxan-4-yl)-1H-pyrazol-5-amine;
N-[(5-chlorothiophen-2-yl)methyl]-4-fluoro-1-(2-methoxybenzoyl)-3-(piperidin-4-yl)-1H-pyrazol-5-amine;
N-[(5-chlorothiophen-2-yl)methyl]-4-fluoro-1-(2-methoxybenzoyl)-3-(pyridin-2-yl)-1H-pyrazol-5-amine;
N-[(5-chlorothiophen-2-yl)methyl]-4-fluoro-1-(2-methoxybenzoyl)-3-phenyl-1H-pyrazol-5-amine;
N-[(5-chlorothiophen-2-yl)methyl]-4-fluoro-1-(2-methoxybenzoyl)-5-(oxan-4-yl)-1H-pyrazol-3-amine;
N-[(5-chlorothiophen-2-yl)methyl]-4-fluoro-1-(3-methyloxetane-3-carbonyl)-3-phenyl-1H-pyrazol-5-amine;
N-[(5-chlorothiophen-2-yl)methyl]-4-fluoro-1-(4-methyloxane-4-carbonyl)-3-(oxan-4-yl)-1H-pyrazol-5-amine;
N-[(5-chlorothiophen-2-yl)methyl]-4-fluoro-1-(4-methyloxane-4-carbonyl)-3-phenyl-1H-pyrazol-5-amine;
N-[(5-chlorothiophen-2-yl)methyl]-4-fluoro-1-(furan-3-carbonyl)-3-(oxan-4-yl)-1H-pyrazol-5-amine;
N-[(5-chlorothiophen-2-yl)methyl]-4-fluoro-1-(furan-3-carbonyl)-3-(piperidin-4-yl)-1H-pyrazol-5-amine;
N-[(5-chlorothiophen-2-yl)methyl]-4-fluoro-1-(furan-3-carbonyl)-3-phenyl-1H-pyrazol-5-amine;
N-[(5-chlorothiophen-2-yl)methyl]-4-fluoro-1-[4-(2-methoxyethoxy)benzoyl]-3-(oxan-4-yl)-1H-pyrazol-5-amine;
N-[(5-chlorothiophen-2-yl)methyl]-4-fluoro-1-[4-(morpholin-4-yl)benzoyl]-3-(oxan-4-yl)-1H-pyrazol-5-amine;
N-[(5-chlorothiophen-2-yl)methyl]-4-fluoro-3-(oxan-4-yl)-1-(thiophene-3-carbonyl)-1H-pyrazol-5-amine;
N-[(5-chlorothiophen-2-yl)methyl]-5-(1-{[5-(dimethylamino)naphthalen-1-yl]sulfonyl}piperidin-4-yl)-4-fluoro-1-(2-methoxybenzoyl)-1H-pyrazol-3-amine;
N-[4-(5-{[(5-chlorothiophen-2-yl)methyl]amino}-4-fluoro-3-(piperidin-4-yl)-1H-pyrazole-1-carbonyl)phenyl]-5-(dimethylamino)naphthalene-1-sulfonamide;
N-[4-(5-{[(5-chlorothiophen-2-yl)methyl]amino}-4-fluoro-3-phenyl-1H-pyrazole-1-carbonyl)phenyl]-5-(dimethylamino)naphthalene-1-sulfonamide;
N-benzyl-4-fluoro-1-(2-methoxybenzoyl)-3-(pyridin-2-yl)-1H-pyrazol-5-amine;
N-benzyl-4-fluoro-1-(2-methoxybenzoyl)-3-phenyl-1H-pyrazol-5-amine;
1-[1-(5-{[(5-chlorothiophen-2-yl)methyl]amino}-4-fluoro-3-(oxan-4-yl)-1H-pyrazole-1-carbonyl)cyclopropyl]methanol; and
[1-(5-{[(5-chlorothiophen-2-yl)methyl]amino}-4-fluoro-3-phenyl-1H-pyrazole-1-carbonyl)cyclopropyl]methanol.

22. A pharmaceutical composition comprising a compound according to claim 1, or a compound selected from:
1-(5-{[(5-chlorothiophen-2-yl)methyl]amino}-3-(1-{[5-(dimethylamino)naphthalen-1-yl]sulfonyl}piperidin-4-yl)-4-fluoro-1H-pyrazol-1-yl)-3-hydroxy-2,2-dimethylpropan-1-one;
1-(5-{[(5-chlorothiophen-2-yl)methyl]amino}-4-fluoro-3-(5-hydroxy-5,6,7,8-tetrahydronaphthalen-2-yl)-1H-pyrazol-1-yl)-2,2-dimethylpropan-1-one;
1-(5-{[(5-chlorothiophen-2-yl)methyl]amino}-4-fluoro-3-(oxan-4-yl)-1H-pyrazol-1-yl)-2,2-dimethylpropan-1-one;
1-(5-{[(5-chlorothiophen-2-yl)methyl]amino}-4-fluoro-3-(oxan-4-yl)-1H-pyrazol-1-yl)-3-hydroxy-2,2-dimethylpropan-1-one;
1-(5-{[(5-chlorothiophen-2-yl)methyl]amino}-4-fluoro-3-(oxan-4-yl)-1H-pyrazol-1-yl)-3-methoxy-2,2-dimethylpropan-1-one;
1-(5-{[(5-chlorothiophen-2-yl)methyl]amino}-4-fluoro-3-(piperidin-4-yl)-1H-pyrazol-1-yl)-2,2-dimethylpropan-1-one;
1-(5-{[(5-chlorothiophen-2-yl)methyl]amino}-4-fluoro-3-(piperidin-4-yl)-1H-pyrazol-1-yl)-2-methoxy-2-methylpropan-1-one;
1-(5-{[(5-chlorothiophen-2-yl)methyl]amino}-4-fluoro-3-(piperidin-4-yl)-1H-pyrazol-1-yl)-3-hydroxy-2,2-dimethylpropan-1-one;
1-(5-{[(5-chlorothiophen-2-yl)methyl]amino}-4-fluoro-3-(piperidin-4-yl)-1H-pyrazol-1-yl)-3-methoxy-2,2-dimethylpropan-1-one;
1-(5-{[(5-chlorothiophen-2-yl)methyl]amino}-4-fluoro-3-phenyl-1H-pyrazol-1-yl)-2,2-dimethylpropan-1-one;
1-(5-{[(5-chlorothiophen-2-yl)methyl]amino}-4-fluoro-3-phenyl-1H-pyrazol-1-yl)-2-hydroxy-2-methylpropan-1-one;

1-(5-{[(5-chlorothiophen-2-yl)methyl]amino}-4-fluoro-3-phenyl-1H-pyrazol-1-yl)-2-methoxy-2-methylpropan-1-one;
1-(5-{[(5-chlorothiophen-2-yl)methyl]amino}-4-fluoro-3-phenyl-1H-pyrazol-1-yl)-3-(2-methoxyethoxy)-2,2-dimethylpropan-1-one;
1-(5-{[(5-chlorothiophen-2-yl)methyl]amino}-4-fluoro-3-phenyl-1H-pyrazol-1-yl)-3-hydroxy-2,2-dimethylpropan-1-one;
1-(5-{[(5-chlorothiophen-2-yl)methyl]amino}-4-fluoro-3-phenyl-1H-pyrazol-1-yl)-3-methoxy-2,2-dimethylpropan-1-one;
1-[4-(5-{[(5-chlorothiophen-2-yl)methyl]amino}-1-(2,2-dimethylpropanoyl)-4-fluoro-1H-pyrazol-3-yl)phenyl]pyrrolidin-2-one;
1-[4-(5-{[(5-chlorothiophen-2-yl)methyl]amino}-1-(2,3-dihydro-1,4-benzodioxine-5-carbonyl)-4-fluoro-1H-pyrazol-3-yl)phenyl]pyrrolidin-2-one;
1-[4-(5-{[(5-chlorothiophen-2-yl)methyl]amino}-4-fluoro-1-(2-methoxybenzoyl)-1H-pyrazol-3-yl)phenyl]-2,2,2-trifluoroethan-1-ol;
1-[4-(5-{[(5-chlorothiophen-2-yl)methyl]amino}-4-fluoro-1-(2-methoxybenzoyl)-1H-pyrazol-3-yl)phenyl]pyrrolidin-2-one;
1-[4-(5-{[(5-chlorothiophen-2-yl)methyl]amino}-4-fluoro-1-(furan-3-carbonyl)-1H-pyrazol-3-yl)phenyl]pyrrolidin-2-one;
1-[5-(benzylamino)-4-fluoro-3-(pyridin-2-yl)-1H-pyrazol-1-yl]-2,2-dimethylpropan-1-one;
1-[5-(benzylamino)-4-fluoro-3-phenyl-1H-pyrazol-1-yl]-2,2-dimethylpropan-1-one;
1-benzoyl-N-[(5-chlorothiophen-2-yl)methyl]-4-fluoro-3-(oxan-4-yl)-1H-pyrazol-5-amine;
1-benzoyl-N-[(5-chlorothiophen-2-yl)methyl]-4-fluoro-5-(oxan-4-yl)-1H-pyrazol-3-amine;
2-(5-{[(5-chlorothiophen-2-yl)methyl]amino}-4-fluoro-3-phenyl-1H-pyrazole-1-carbonyl)phenyl 5-(dimethylamino)naphthalene-1-sulfonate;
4-(5-{[(5-chlorothiophen-2-yl)methyl]amino}-4-fluoro-3-phenyl-1H-pyrazole-1-carbonyl)phenyl 5-(dimethylamino)naphthalene-1-sulfonate;
4-[4-(5-{[(5-chlorothiophen-2-yl)methyl]amino}-1-(2,2-dimethylpropanoyl)-4-fluoro-1H-pyrazol-3-yl)phenyl]morpholin-3-one;
6-(5-{[(5-chlorothiophen-2-yl)methyl]amino}-1-(2,2-dimethylpropanoyl)-4-fluoro-1H-pyrazol-3-yl)-1,2,3,4-tetrahydronaphthalen-1-one;
6-(5-{[(5-chlorothiophen-2-yl)methyl]amino}-4-fluoro-1-(2-methoxybenzoyl)-1H-pyrazol-3-yl)-1,2,3,4-tetrahydronaphthalen-1-ol;
6-(5-{[(5-chlorothiophen-2-yl)methyl]amino}-4-fluoro-1-(2-methoxybenzoyl)-1H-pyrazol-3-yl)-1,2,3,4-tetrahydronaphthalen-1-one;
N-[(5-chlorothiophen-2-yl)methyl]-1-(2,3-dihydro-1,4-benzodioxine-5-carbonyl)-4-fluoro-3-(oxan-4-yl)-1H-pyrazol-5-amine;
N-[(5-chlorothiophen-2-yl)methyl]-1-(2,3-dihydro-1,4-benzodioxine-5-carbonyl)-4-fluoro-3-(piperidin-4-yl)-1H-pyrazol-5-amine;
N-[(5-chlorothiophen-2-yl)methyl]-1-(2,3-dihydro-1,4-benzodioxine-5-carbonyl)-4-fluoro-3-phenyl-1H-pyrazol-5-amine;
N-[(5-chlorothiophen-2-yl)methyl]-1-(2,3-dihydro-1,4-benzodioxine-5-carbonyl)-4-fluoro-5-(oxan-4-yl)-1H-pyrazol-3-amine;
N-[(5-chlorothiophen-2-yl)methyl]-1-(2,4-dimethoxybenzoyl)-4-fluoro-3-(oxan-4-yl)-1H-pyrazol-5-amine;
N-[(5-chlorothiophen-2-yl)methyl]-1-(2,4-dimethoxybenzoyl)-4-fluoro-3-(piperidin-4-yl)-1H-pyrazol-5-amine;
N-[(5-chlorothiophen-2-yl)methyl]-1-(2,4-dimethoxybenzoyl)-4-fluoro-3-phenyl-1H-pyrazol-5-amine;
N-[(5-chlorothiophen-2-yl)methyl]-1-(2,4-dimethoxybenzoyl)-4-fluoro-5-(oxan-4-yl)-1H-pyrazol-3-amine;
N-[(5-chlorothiophen-2-yl)methyl]-3-(1-{[5-(dimethylamino)naphthalen-1-yl]sulfonyl}piperidin-4-yl)-4-fluoro-1-(2-methoxybenzoyl)-1H-pyrazol-5-amine;
N-[(5-chlorothiophen-2-yl)methyl]-4-fluoro-1-(2-methoxybenzoyl)-3-(oxan-4-yl)-1H-pyrazol-5-amine;
N-[(5-chlorothiophen-2-yl)methyl]-4-fluoro-1-(2-methoxybenzoyl)-3-(piperidin-4-yl)-1H-pyrazol-5-amine;
N-[(5-chlorothiophen-2-yl)methyl]-4-fluoro-1-(2-methoxybenzoyl)-3-(pyridin-2-yl)-1H-pyrazol-5-amine;
N-[(5-chlorothiophen-2-yl)methyl]-4-fluoro-1-(2-methoxybenzoyl)-3-phenyl-1H-pyrazol-5-amine;
N-[(5-chlorothiophen-2-yl)methyl]-4-fluoro-1-(2-methoxybenzoyl)-5-(oxan-4-yl)-1H-pyrazol-3-amine;
N-[(5-chlorothiophen-2-yl)methyl]-4-fluoro-1-(3-methyloxetane-3-carbonyl)-3-phenyl-1H-pyrazol-5-amine;
N-[(5-chlorothiophen-2-yl)methyl]-4-fluoro-1-(4-methyloxane-4-carbonyl)-3-(oxan-4-yl)-1H-pyrazol-5-amine;
N-[(5-chlorothiophen-2-yl)methyl]-4-fluoro-1-(4-methyloxane-4-carbonyl)-3-phenyl-1H-pyrazol-5-amine;
N-[(5-chlorothiophen-2-yl)methyl]-4-fluoro-1-(furan-3-carbonyl)-3-(oxan-4-yl)-1H-pyrazol-5-amine;
N-[(5-chlorothiophen-2-yl)methyl]-4-fluoro-1-(furan-3-carbonyl)-3-(piperidin-4-yl)-1H-pyrazol-5-amine;
N-[(5-chlorothiophen-2-yl)methyl]-4-fluoro-1-(furan-3-carbonyl)-3-phenyl-1H-pyrazol-5-amine;
N-[(5-chlorothiophen-2-yl)methyl]-4-fluoro-1-[4-(2-methoxyethoxy)benzoyl]-3-(oxan-4-yl)-1 H-pyrazol-5-amine;
N-[(5-chlorothiophen-2-yl)methyl]-4-fluoro-1-[4-(morpholin-4-yl)benzoyl]-3-(oxan-4-yl)-1H-pyrazol-5-amine;
N-[(5-chlorothiophen-2-yl)methyl]-4-fluoro-3-(oxan-4-yl)-1-(thiophene-3-carbonyl)-1H-pyrazol-5-amine;
N-[(5-chlorothiophen-2-yl)methyl]-5-(1-{[5-(dimethylamino)naphthalen-1-yl]sulfonyl}piperidin-4-yl)-4-fluoro-1-(2-methoxybenzoyl)-1H-pyrazol-3-amine;
N-[4-(5-{[(5-chlorothiophen-2-yl)methyl]amino}-4-fluoro-3-(piperidin-4-yl)-1H-pyrazole-1-carbonyl)phenyl]-5-(dimethylamino)naphthalene-1-sulfonamide;
N-[4-(5-{[(5-chlorothiophen-2-yl)methyl]amino}-4-fluoro-3-phenyl-1H-pyrazole-1-carbonyl)phenyl]-5-(dimethylamino)naphthalene-1-sulfonamide;
N-benzyl-4-fluoro-1-(2-methoxybenzoyl)-3-(pyridin-2-yl)-1H-pyrazol-5-amine;
N-benzyl-4-fluoro-1-(2-methoxybenzoyl)-3-phenyl-1H-pyrazol-5-amine;
[1-(5-{[(5-chlorothiophen-2-yl)methyl]amino}-4-fluoro-3-(oxan-4-yl)-1H-pyrazole-1-carbonyl)cyclopropyl]methanol; and
[1-(5-{[(5-chlorothiophen-2-yl)methyl]amino}-4-fluoro-3-phenyl-1H-pyrazole-1-carbonyl)cyclopropyl]methanol,
and a pharmaceutically acceptable excipient.

23. A method for treating a disease or disorder responsive to inhibition of thrombin in a subject, comprising administering a compound according to claim 1 or a pharmaceutical composition according to claim 22, to a subject in need thereof in an amount effective to treat said disease or disorder.

24. The method according to claim 23, wherein said disease or disorder is at least one of a thrombotic disorder, or a disease or disorder involving a blood clot thrombus.

25. The method according to claim 24, wherein said thrombotic disorder comprises at least one of acute coronary syndrome, thromboembolism, and thrombosis.

26. The method according to claim 23, wherein said disease or disorder is one or more selected from the group consisting of fibrosis, Alzheimer's Disease, multiple sclerosis, pain, cancer, and inflammation.

27. The method according to claim 23, wherein said compound acts by inhibiting thrombin.

28. The pharmaceutical composition of claim 22, for use in a method of treating a disease or disorder responsive to inhibition of thrombin in a subject, comprising administering to a subject in need thereof an amount of the composition effective to treat said disease or disorder.

29. The method according to claim 25, wherein the thromboembolism comprises at least one of venous thromboembolism, arterial thromboembolism, and cardiogenic thromboembolism.

30. The method according to claim 29, wherein the venous thromboembolism comprises at least one of deep vein thrombosis and pulmonary embolism.

31. The method according to claim 30, wherein the at least one of deep vein thrombosis and pulmonary embolism occurs following a medical procedure.

32. The method according to claim 24, wherein said thrombotic disorder involves dysfunctional coagulation or disseminated intravascular coagulation.

33. The method according to claim 32, wherein the subject is undergoing percutaneous coronary intervention (PCI).

34. The method according to claim 24, wherein said thrombotic disease or disorder involves a blood clot thrombus and further involves at least one of stroke and one or more transient ischemic attacks (TIA).

35. The method according to claim 34, wherein said thrombotic disease or disorder involving a blood clot thrombus further involves stroke and wherein the subject has non-valvular atrial fibrillation.

36. The method according to claim 24, wherein said thrombotic disease or disorder involves a blood clot thrombus and further involves pulmonary hypertension.

37. The method according to claim 36, wherein the pulmonary hypertension is caused by at least one of one or more left heart disorder and chronic thromboembolic disease.

38. The method according to claim 36, wherein the pulmonary hypertension is associated with at least one of one or more lung disease, including pulmonary fibrosis (idiopathic or otherwise), and hypoxia.

39. The method according to claim 23, wherein the subject has had at least one previous myocardial infarction.

40. The method according to claim 29, wherein the venous thromboembolism is associated with at least one of formation of a thrombus within a vein associated with one or more acquired or inherited risk factors and embolism of peripheral veins caused by a detached thrombus.

41. The method according to claim 40, wherein the one or more risk factors comprise a previous venous thromboembolism.

42. The method according to claim 29, wherein the cardiogenic thromboembolism is due to formation of a thrombus in the heart associated with at least one of cardiac arrhythmia, a heart valve defect, prosthetic heart valves or heart disease, and embolism of peripheral arteries caused by a detached thrombus.

43. The method according to claim 42, wherein the detached thrombus is in the brain (ischemic stroke).

44. The method according to claim 43, wherein the detached thrombus causes a transient ischemic attack (TIA).

45. The method according to claim 42, wherein the cardiogenic thromboembolism is due to non-valvular atrial fibrillation.

46. The method according to claim 25, wherein the thrombosis is arterial thrombosis.

47. The method according to claim 46, wherein the arterial thrombosis is due to one or more underlying atherosclerotic processes in the arteries.

48. The method according to claim 47, wherein the one or more underlying atherosclerotic processes in the arteries cause at least one of obstruction or occlusion of an artery, myocardial ischemia (angina pectoris, acute coronary syndrome), myocardial infarction, obstruction or occlusion of a peripheral artery (ischemic peripheral artery disease), and obstruction or occlusion of the artery after a procedure on a blood vessel (reocclusion or restenosis after transluminal coronary angioplasty, reocclusion or restenosis after percutaneous transluminal angioplasty of peripheral arteries).

49. The method according to claim 23, wherein the treatment further comprises an adjunct therapy.

50. The method according to claim 49, wherein the subject has myocardial infarction, and the adjunct therapy is in conjunction with thrombolytic therapy.

51. The method according to claim 49, wherein the subject has at least one of unstable angina pectoris, thrombosis, and heparin-induced thrombocytopenia, and the adjunct therapy is in combination with antiplatelet therapy.

52. The method according to claim 49, wherein the subject has non-valvular atrial fibrillation, and the adjunct therapy is in conjunction with other therapies.

* * * * *